United States Patent
Weiser et al.

(10) Patent No.: US 9,505,873 B2
(45) Date of Patent: *Nov. 29, 2016

(54) PHOTOPOLYMER FORMULATIONS HAVING A LOW CROSSLINKING DENSITY

(75) Inventors: Marc-Stephan Weiser, Leverkusen (DE); Thomas Roelle, Leverkusen (DE); Friedrich-Karl Bruder, Krefeld (DE); Thomas Fäcke, Leverkusen (DE); Dennis Hönel, Zülpich (DE)

(73) Assignee: Covestro Deutschland AG, Leverkusen (DE)

( * ) Notice: Subject to any disclaimer, the term of this patent is extended or adjusted under 35 U.S.C. 154(b) by 523 days.

This patent is subject to a terminal disclaimer.

(21) Appl. No.: 12/569,224

(22) Filed: Sep. 29, 2009

(65) Prior Publication Data

US 2010/0087564 A1    Apr. 8, 2010

(30) Foreign Application Priority Data

Oct. 1, 2008 (EP) ..................................... 08017276

(51) Int. Cl.
| | | |
|---|---|---|
| G03H 1/02 | (2006.01) | |
| G03H 1/26 | (2006.01) | |
| G11B 7/24044 | (2013.01) | |
| C08G 18/40 | (2006.01) | |
| C08G 18/78 | (2006.01) | |
| C07C 323/43 | (2006.01) | |
| C07F 9/18 | (2006.01) | |
| C08G 18/42 | (2006.01) | |
| C08G 18/48 | (2006.01) | |
| C08G 18/73 | (2006.01) | |
| G03F 7/00 | (2006.01) | |
| G03F 7/027 | (2006.01) | |
| G03F 7/032 | (2006.01) | |
| G03F 7/035 | (2006.01) | |
| G11B 7/245 | (2006.01) | |

(52) U.S. Cl.
CPC ......... *C08G 18/7837* (2013.01); *C07C 323/43* (2013.01); *C07F 9/18* (2013.01); *C08G 18/4277* (2013.01); *C08G 18/4837* (2013.01); *C08G 18/4854* (2013.01); *C08G 18/73* (2013.01); *C08G 18/7887* (2013.01); *G03F 7/001* (2013.01); *G03F 7/027* (2013.01); *G03F 7/032* (2013.01); *G03F 7/035* (2013.01); *G11B 7/245* (2013.01); *G11B 7/24044* (2013.01); *G03H 2240/24* (2013.01); *G03H 2260/12* (2013.01); *G03H 2260/30* (2013.01)

(58) Field of Classification Search
None
See application file for complete search history.

(56) References Cited

U.S. PATENT DOCUMENTS 4,942,112 A * 7/1990 Monroe et al. ............. 430/282.1
5,462,797 A * 10/1995 Williams et al. ............. 428/345

(Continued)

FOREIGN PATENT DOCUMENTS

EP  0223587 B1  5/1987
EP  0352774 A1  1/1990

(Continued)

*Primary Examiner* — Martin Angebranndt
(74) *Attorney, Agent, or Firm* — Drinker Biddle & Reath LLP

(57) ABSTRACT

The invention relates to photopolymer formulations based on a polymeric network as a matrix and at least one photopolymerizable monomer dissolved therein and to a method for the production of holographic media from such photopolymers and to the use thereof.

15 Claims, 2 Drawing Sheets

(56) References Cited

U.S. PATENT DOCUMENTS

| | | | |
|---|---|---|---|
| 5,470,813 A * | 11/1995 | Le-Khac | 502/175 |
| 5,916,987 A | 6/1999 | Kobayashi et al. | |
| 6,103,454 A | 8/2000 | Dhar et al. | |
| 6,165,648 A * | 12/2000 | Colvin et al. | 430/1 |
| 6,706,354 B1 * | 3/2004 | Otaki | G03H 1/0252 283/108 |
| 6,780,546 B2 | 8/2004 | Trentler et al. | |
| 6,794,471 B2 | 9/2004 | Ohkuma et al. | |
| 6,939,648 B2 | 9/2005 | Dhar et al. | |
| 7,981,987 B2 * | 7/2011 | Stockel et al. | 526/301 |
| 8,329,773 B2 * | 12/2012 | Facke | G03F 7/001 430/269 |
| 8,361,678 B2 * | 1/2013 | Weiser | C08G 18/4866 430/1 |
| 8,852,829 B2 * | 10/2014 | Weiser | C08G 18/089 359/3 |
| 8,889,321 B2 * | 11/2014 | Bruder | G11B 7/24044 359/3 |
| 8,921,012 B2 * | 12/2014 | Weiser | G03F 7/001 359/3 |
| 9,073,296 B2 * | 7/2015 | Facke | B32B 27/40 |
| 2002/0142227 A1 * | 10/2002 | Dhar | G03F 7/001 430/1 |
| 2003/0206320 A1 * | 11/2003 | Cole et al. | 359/15 |
| 2005/0222365 A1 * | 10/2005 | Mager et al. | 528/73 |
| 2006/0115740 A1 * | 6/2006 | Hayase et al. | 430/1 |
| 2007/0072124 A1 | 3/2007 | Yamada | |
| 2007/0077498 A1 | 4/2007 | Yumoto et al. | |
| 2007/0224541 A1 * | 9/2007 | Hayase et al. | 430/280.1 |
| 2008/0145766 A1 * | 6/2008 | Mikoshiba et al. | 430/2 |
| 2008/0311482 A1 * | 12/2008 | Stockel et al. | 430/2 |
| 2008/0311483 A1 * | 12/2008 | Stockel et al. | 430/2 |
| 2009/0062419 A1 * | 3/2009 | Stockel et al. | 522/109 |
| 2009/0185470 A1 * | 7/2009 | Stoeckel et al. | 369/103 |
| 2010/0020373 A1 * | 1/2010 | Askham | 359/3 |
| 2010/0086861 A1 * | 4/2010 | Weiser et al. | 430/2 |
| 2014/0295329 A1 * | 10/2014 | Weiser | G11B 7/2542 430/2 |

FOREIGN PATENT DOCUMENTS

| | | |
|---|---|---|
| EP | 0945762 A1 | 9/1999 |
| WO | WO-2008/125199 A1 | 10/2008 |

* cited by examiner

PHOTOPOLYMER FORMULATIONS HAVING A LOW CROSSLINKING DENSITY

RELATED APPLICATIONS

This application claims benefit to European Patent Application No. 08017276.0, filed Oct. 1, 2008, which is incorporated herein by reference in its entirety for all useful purposes.

BACKGROUND OF THE INVENTION

The invention relates to photopolymer formulations based on a polymeric network as matrix and at least one photopolymerizable monomer dissolved therein and to a process for the production of holographic media from such photopolymers and to the use thereof. Prior to exposure to light, the photopolymer formulation has, as a measure of the crosslinking density, a particular average molecular weight $M_C$ of the segments bridging two polymer strands or a particular ratio Q of this crosslinking density to the molar mass $M_{Mo}$ of the dissolved writing monomer, expressed as $Q=M_C/M_{Mo}$.

Photopolymers are materials which can be exposed by means of the superposition of two coherent light sources. A three-dimensional structure forms in the photopolymers and can generally be written in the material as a result of a regional change in the refractive index. Such structures are referred to as holograms, which can also be described as diffractive optical elements. Which optical functions such a hologram forms depends on the specific exposure.

For the use of photopolymers as carriers of holograms for optical applications in the visible ($\lambda$=400-800 nm) and in the near UV range ($\lambda$=300-400 nm), colourless materials having a high diffraction effect are required as a rule after the exposure. Since the beginning of holography, silver halide films have been used for this purpose, in particular those having a high resolution. Dichromate gelatin (DCG), dichromate salt-containing gelatin films or mixed forms of silver halide and DCG are also used. Both materials require a chemical aftertreatment for the formation of a hologram, which, for industrial processes, gives rise to additional costs and necessitates the handling of chemical developer solutions. In addition, wet chemical processes result in swelling and subsequently shrinkage of the film, which can lead to colour shifts in the holograms, which is undesired.

U.S. Pat. No. 4,959,284 (Dupont) describes photopolymers which, inter alia, consist of a thermoplastic soluble in organic solvents, such as polyvinyl acetate, cellulose acetobutyrate or polymethyl methacrylate-styrene copolymers, a photoinitiator and at least one vinylcyclopropane. In addition, EP352774A1 (Dupont) describes monomers containing other vinyl groups, such as N-vinylpyrrolidone, phenoxyethyl acrylate and acrylates of triols, such as trimethylolpropane (TMPTA) and ethoxylated trimethylolpropane (TMPEOTA) or other acrylates or acrylamides. It is known in the industry that such photopolymers give usable holograms only after a relatively long thermal treatment. O'Neill et al. (Applied Optics, Vol. 41, No. 5, page 845 et seq., 2002), in their review article, discuss not only the abovementioned materials but also photopolymers which are obtainable from thermoplastics and acrylamide. In addition to the disadvantageous toxicological profile of acrylamide, such products do not give light holograms.

Holographically active materials into which it is possible to incorporate dyes which change their photosensitivity under the influence of light (Luo et al, Optics Express, Vol. 13, No. 8, 2005, page 3123) are also known. Similarly, Bieringer (Springer Series in Optical Sciences (2000), 76, pages 209-228.) describes so-called photoaddressable polymers which likewise polymer-bound dyes which can be isomerized under the influence of light. In both classes of substances, holograms can be incorporated by exposure and these materials can be used for holographic data storage. However, these products are of course highly coloured and hence not suitable for the applications described above.

More recently, photopolymers which are contained not from thermoplastics but from crosslinked polymers were also described: thus US 020070077498 (Fuji) describes 2,4,6-tribromophenyl acrylate which is dissolved in a polyurethane matrix. U.S. Pat. No. 6,103,454 (InPhase) likewise describes a polyurethane matrix having polymerizable components, such as 4-chlorophenyl acrylate, 4-bromostryrene and vinylnaphthalene. These formulations, too, were developed for holographic data storage, a holographic application in which many, but also very weak, holograms readable using electronic detectors are written and read. Common to them is the fact that the highly refracting photopolymerizable monomers are present in solution in a matrix having a low refractive index. For optical applications in the entire visible ($\lambda$=400-800 nm) and the near UV range ($\lambda$=300-400 nm), such formulations are likewise not suitable.

It was an object of the present invention to develop photopolymers for the applications as holographic media which can be processed without thermal or wet chemical aftertreatment and with which colourless holograms having a high diffraction efficiency and great brightness can be produced after exposure.

In addition to the physical properties, however, the processability and compatibility with other components are also important. Thus, organic materials which are obtained by photopolymerization, generally as homo- or copolymers of highly refracting monomers, play an important role, for example for the production of optical components, such as lenses, prisms and optical coatings (U.S. Pat. No. 5,916,987) or for the production of a contrast in holographic materials (U.S. Pat. No. 6,780,546). For such and similar applications, there is a need to be able to adjust the refractive index in a targeted manner, for example by admixing components having a high or low refractive index, and to be able to vary said refractive index over ranges. This can lead to photopolymers in which highly refracting photopolymerizable monomers are dissolved in matrices having a low refractive index or conversely photopolymerizable monomers having a low refractive index are present in solution in the highly refracting matrices.

For the abovementioned fields of use, polymers of olefinically unsaturated compounds, such as, preferably, (meth) acrylates, are typically employed. In order to achieve a refractive index of 1.5 or higher, halogen-substituted aromatic (meth)acrylates or special alkyl methacrylates described in U.S. Pat. No. 6,794,471 can be used. In particular the latter are disadvantageous owing to their complicated preparation.

The suitability of substituted phenyl isocyanate-based urethane acrylates for the preparation of corresponding polymers was described by Bowman (Polymer 2005, 46, 4735-4742).

The non-prior-published WO application PCT/EP2008/002464 discloses (meth)acrylates having a refractive index at $\lambda$=532 nm of at least 1.5, which are suitable for production of optical data media, in particular those for holographic storage methods, and are based on industrially available raw materials. In this context, phenyl isocyanate-based compounds are also known, these always being based on unsubstituted phenyl rings on the isocyanate side.

In photopolymer formulations, highly refracting acrylates play a decisive role as a contrast-imparting component (U.S. Pat. No. 6,780,546). The interference field of signal light beam and reference light beam (in the simplest case two plane waves) is formed by the local photopolymerization at locations of high intensity in the interference field by the highly refracting acrylates in a refractive index grating which contains all information of the signal (the hologram). By illuminating the hologram only with the reference light beam, the signal can then be reconstructed again. The maximum strength of the signal thus reconstructed in relation to the strength of the incident reference light is referred to as Diffraction Efficiency, DE below. In the simplest case of a hologram which forms from the overlap of two plane waves, the DE is obtained from the quotient of the intensity of the light diffracted on reconstruction and the sum of the intensities of incident reference light and diffracted light. The higher the DE, the more efficient is a hologram with respect to the necessary quantity of light of the reference light which is necessary to make the signal visible with a fixed brightness. Highly refracting acrylates are capable of producing refractive index gratings having a high amplitude Δn between regions with the lowest refractive index and regions with the highest refractive index and thus permitting holograms with high DE in photopolymer formulations. (The refractive index contrast □n which results on writing a volume hologram by means of the overlap of two plane waves is obtained from the following refractive index variation $n(x)=n_0+\Delta n\cdot\cos(K\cdot x)$, where K represents the magnitude of the grating vector which points in the direction of the x-axis and $n_0$ represents the mean refractive index. See, for example, Hariharan Optical Holography, Principles, Techniques and Applications, Cambridge University Press, 1991 page 44.)

U.S. Pat. No. 6,939,648B describes optical articles obtained from photopolymer formulations which are based on a crosslinked polyurethane matrix and have a modulus of elasticity E of at least 0.1 MPa, the thickness of the photopolymer layer being greater than 200 μm. It is disclosed that, the greater the modulus of elasticity, the more preferred the photopolymer formulation is said to be. It is not specified how the modulus of elasticity is measured and how it is to be understood in relation to the topology and dynamic properties of the matrix polymer strands, i.e. whether it characterizes the photopolymer state crosslinked in a rubber-like manner or the photopolymer state solidified in a glassy manner. The relationship between crosslinking density, writing monomer molecular weight and the holographic performance in the case of individual strong holograms is not disclosed, in particular not for reflection holograms. On the contrary, the preferred direction described in the abovementioned application leads to higher modulus of elasticity and, when writing individual strong holograms, to a deterioration in the holographic performance, as can be seen from the examples disclosed here.

A known procedure for optimizing the performance of photopolymers in holographic applications is therefore to increase the difference between the refractive indices of the matrix polymer and of the writing monomer dissolved therein, for example by dissolving highly refracting writing monomers in matrices having a low refractive index or using writing monomers having a low refractive index in highly refracting matrices.

If the matrix is formed as a polymeric network, the mechanical, optical, thermal and thermodynamic properties of the photopolymer can be established in a targeted manner within wide limits by the choice of the network-building repeating units and the functionalities thereof. The prior art described above does not disclose whether and to what extent the crosslinking density of such photopolymers can decisively influence the performance in holographic media.

It has now surprisingly been found that photopolymer formulations based on a matrix which represents a polymeric network and at least one photopolymerizable monomer dissolved therein produce refractive index gratings having high amplitude (Δn) between regions with the lowest refractive index and regions with the highest refractive index in holographic media in particular when a low crosslinking density of the photopolymer formulation is present prior to the exposure to light. Such photopolymer formulations are therefore particularly suitable for producing bright, visual holograms having high diffraction efficiency in holographic media as described above. Visual holograms comprise all holograms which can be recorded by methods known to the person skilled in the art, including, inter alia, in-line (Gabor) holograms, off-axis holograms, full-aperture transfer holograms, white light transmission holograms ("rainbow holograms"), Denisyuk holograms, off-axis reflection holograms, edge-lit holograms and holographic stereograms; reflection holograms, Denisyuk holograms and transmission holograms are preferred.

EMBODIMENTS OF THE INVENTION

An embodiment of the present invention is a photopolymer formulation comprising a three-dimensionally crosslinked organic polymer A) or the precursors thereof as a matrix, a compound B) comprising groups that react with ethylenically unsaturated compounds via polymerization under the action of actinic radiation and is present in solution or dispersion in said matrix, and C) at least one photoinitiator, wherein the network density of said three-dimensionally crosslinked organic polymer, expressed as the average molecular weight $M_C$ of the segments bridging two polymer strands, is at least 2685 g/mol.

Another embodiment of the present invention is the above photopolymer formulation, wherein the network density of said three-dimensionally crosslinked organic polymer is in the range of from 7500 to 55000 g/mol.

Another embodiment of the present invention is the above photopolymer formulation, wherein the ratio Q of the molecular weight $M_C$ to the number average molecular weight $M_{Mo}$ of B) is greater than 3.30.

Another embodiment of the present invention is the above photopolymer formulation, wherein the ratio Q is greater than 10.00.

Another embodiment of the present invention is the above photopolymer formulation, wherein said three-dimensionally crosslinked organic polymers comprise urethane groups.

Another embodiment of the present invention is the above photopolymer formulation, wherein said three-dimensionally crosslinked organic polymers are composed of an isocyanate component a) and an isocyanate-reactive component b).

Another embodiment of the present invention is the above photopolymer formulation, wherein A) comprises an isocyanate component a) and an isocyanate-reactive component b).

Another embodiment of the present invention is the above photopolymer formulation, wherein component a) comprises a polyisocyanate based on HDI with isocyanurate and/or iminooxadiazinedione structures or a prepolymer having an NCO functionality of from 2 to 5 with allophanate and/or urethane structures based on HDI and/or TMDI and a polyether polyol, polyester polyol, and/or polycarbonate polyol.

Another embodiment of the present invention is the above photopolymer formulation, wherein component b) comprises a polypropylene oxide, a polyethylene oxide, and/or combinations thereof in the form of a random or block copolymer and/or a block copolymer of the abovementioned type which additionally comprises tetrahydrofuran, butylene oxide, or ε-caprolactone as monomer units, wherein the OH functionality is from 1.5 to 6 and the number average molecular weight is from 200 to 18000 g/mol.

Another embodiment of the present invention is the above photopolymer formulation, wherein said compound of B) has a refractive index $n_D^{20}$ of greater than 1.54.

Another embodiment of the present invention is the above photopolymer formulation, wherein said compound of B) comprise acrylate and/or methacrylate groups as radiation-curing groups.

Yet another embodiment of the present invention is a medium suitable for recording visual holograms produced from the above photopolymer formulation.

Yet another embodiment of the present invention is an optical element, image, or representation produced from the above medium.

Yet another embodiment of the present invention is a method for exposing the above medium comprising selectively polymerizing writing monomers with actinic radiation.

DESCRIPTION OF THE INVENTION

Figure 1:
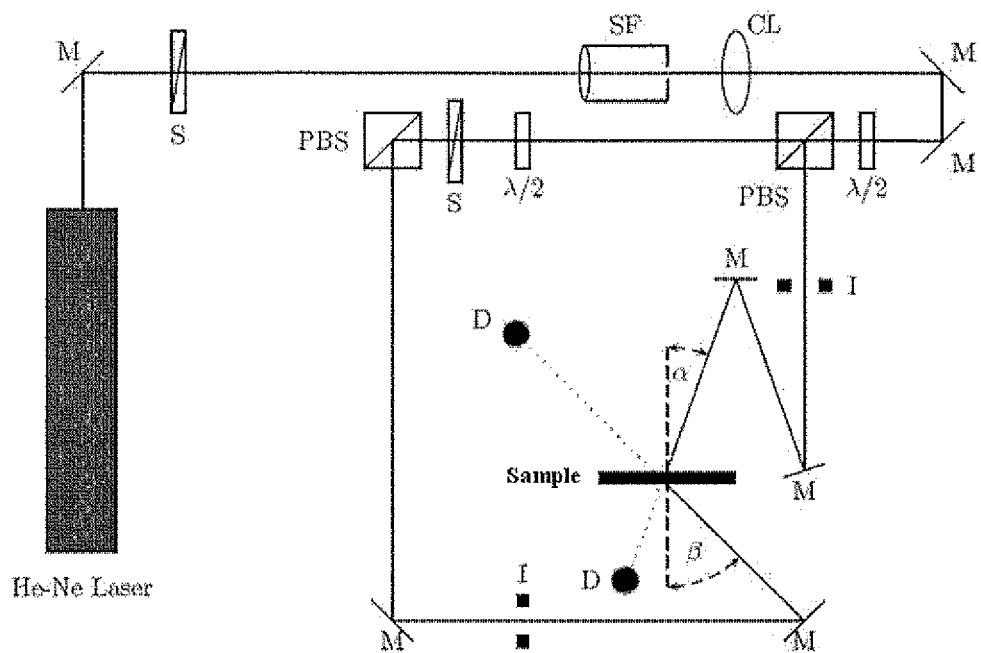
FIG. 1 depicts the holographic experimental setup with which the diffraction efficiency. (DE) of the media was measured.

The present invention therefore relates to photopolymer formulations comprising three-dimensionally crosslinked organic polymers A) as a matrix and compounds B) which have groups reacting with ethylenically unsaturated compounds with polymerization under the action of actinic radiation (radiation-curing groups) and are present in solution or dispersion in this matrix and C) at least one photoinitiator, characterized by a network density of the organic polymer, expressed by the average molecular weight $M_C$ of the segments bridging two polymer strands, of 2685 g/mol to 55 000 g/mol.

The present invention furthermore relates to holographic media which are obtainable from photopolymer formulations according to the invention.

Radiation-curable groups in the context of the present invention are all functional groups which react with olefinically unsaturated compounds with polymerization under the action of actinic radiation. These are, for example, vinyl ether ($CH_2$=CH—O—), maleyl (cis-HOOC—C=C—CO—O—), fumaryl (trans-HOOC—C=C—CO—O—), maleimide, dicyclopentadienyl, acrylamide ($CH_2$=CH—(CO)—NH—), methacrylamide ($CH_2$=$CCH_3$—(CO)—NH—), acrylate ($CH_2$=CH—(CO)—O—) and methacrylate groups ($CH_2$=$CH_3$—(CO)—O—).

Actinic radiation is understood as meaning electromagnetic, ionizing radiation, in particular electron beams, UV radiation and visible light (Roche Lexikon Medizin [Roche Medical Lexicon], 4$^{th}$ edition; Urban & Fischer Verlag, Munich 1999).

The determination of the average molecular weight $M_C$ is effected via the determination of the plateau modulus $G_0$ in an oscillation rheometer, the following known relationship (M. Doi, S. F. Edwards, The Theory of Polymer Dynamics, Oxford Science Publications, 1986) being used:

$$G_0 = \frac{\rho \cdot R \cdot T}{M_C}$$

R is the Avogadro constant, T the absolute temperature in Kelvin and ρ is the mass density.

Preferably, the segments bridging two polymer strands have average molecular weights $M_C$ of 2685 g/mol to 55 000 g/mol, particularly preferably of 3400 g/mol to 55 000 g/mol, very particularly preferably of 7500 g/mol of 55 000 g/mol.

It is preferable if $M_C$ corresponds to the abovementioned values and moreover the ratio Q of $M_C$ to the number average molecular weight $M_{Mo}$ of all radiation-curable compounds used in B) is greater than 3.30, particularly preferably greater than 4.13, very particularly preferably greater than 10.00.

In addition to the components A) and B), the photopolymer formulations according to the invention may contain photoinitiator systems C) which of at least one light-absorbing component and optionally at least one further component which optionally absorbs the energy of the excited state of the light-absorbing compound and thus initiates the start of the photopolymerization. In suitable systems, the start of the photopolymerization can also be initiated by the light-absorbing component itself.

Further components may be stabilizers which, for example, improve the shelf-life of the components of the photopolymer formulation or stabilizers which, for example, improve the stability of the holographic media produced from the photopolymer formulations according to the invention to ambient light, temperature and moisture or additives such as, for example, solvents or such as, for example, release agents, which facilitate the processing of the photopolymer formulations according to the invention to give the corresponding holographic media or improve or actually permit the usability of the holographic media in the final application.

The matrix (component A) is a solid polymer having a three-dimensional network structure, which is formed in situ from the reaction of one or more precursors by a "curing step". The reaction for the formation of the matrix is initiated by an initiation reaction. The precursors may consist of one type of monomer, a plurality of monomers, one type of oligomer, a plurality of oligomers or a mixture of monomers and oligomers. It is also possible for one or more of the precursors to carry more than one type of functional group as reacting in the curing step. In order to ensure good miscibility of the precursor(s) with the other constituents of the formulation, said precursor is preferably liquid in a certain temperature range between −50° C. and 80° C. Particularly preferably, the mixture can be prepared at temperatures between 15° C. and 75° C. in a period of less than 200 minutes. The matrix has a glass transition temperature which is sufficiently low to permit chemical reactions and sufficient diffusion of the component B) during the writing of the hologram. A temperature range between −130° C. and 80° C. is preferred. Examples of chemical reactions for producing such a matrix are cationic epoxide polymerization, cationic polymerization of vinyl ethers, cationic polymerization of alkenyl ethers, cationic Allen polymerization, cationic ketene-acetal polymerization, addition polymerization of epoxides and amines or epoxides and thiols, poly-Michael addition (addition polymerization of unsaturated esters with amines or thiols), addition polymerization of silicone hydrides with vinyl compounds via hydrosilylation and polyaddition of isocyanates with OH- or NH-functional compounds (by polyurethane or polyurea formation). Various of the reactions described can be accelerated by the presence of suitable catalysts.

Preferred three-dimensionally crosslinked organic polymers are those which have urethane groups.

Particularly preferred three-dimensionally crosslinked organic polymers are those which are composed of an isocyanate component a) and an isocyanate-reactive component b) as precursors.

Suitable compounds of the polyisocyanate component a) are all aliphatic, cycloaliphatic, aromatic or araliphatic di- and triisocyanates known per se to the person skilled in the art, it being unimportant whether they were obtained by means of phosgenation or by phosgene-free processes. In addition, the higher molecular weight secondary products well known per se to the person skilled in the art (oligo- and polyisocyanates) of monomeric di- and/or triisocyanates having a urethane, urea, carbodiimide, acylurea, isocyanurate, allophanate, biuret, oxadiazinetrione, uretdione, iminooxadiazinedione structure can also be used in each case individually or in any desired mixtures with one another.

For example, suitable monomeric di- or triisocyanates are butylene diisocyanate, hexamethylene diisocyanate (HDI), isophorone diisocyanate (IPDI), trimethylhexamethylene diisocyanate (TMDI), 1,8-diisocyanato-4-(isocyanatomethyl)octane, isocyanatomethyl-1,8-octane diisocyanate (TIN), 2,4- and/or 2,6-toluene diisocyanate.

Also possible is the use of isocyanate-functional prepolymers having a urethane, allophanate or biuret structure as compounds of component a), as can be obtained in a manner well known per se by reaction of the abovementioned di-, tri- or polyisocyanates in excess with hydroxy- or amino-functional compounds. Any unconverted starting isocyanate can subsequently be removed in order to obtain products having a low monomer content. For accelerating the prepolymer formation, the use of catalysts well known per se to the person skilled in the art from polyurethane chemistry may be helpful.

Suitable hydroxy- or amino-functional compounds for the prepolymer synthesis are typically low molecular weight short-chain aliphatic, araliphatic, or cycloaliphatic diols, trials and/or higher polyols, i.e. containing 2 to 20 carbon atoms.

Examples of dials are ethylene glycol, diethylene glycol, triethylene glycol, tetraethylene glycol, dipropylene glycol, tripropylene glycol, 1,2-propanediol, 1,3-propanediol, 1,4-butanediol, neopentylglycol, 2-ethyl-2-butylpropanediol, trimethylpentanediol, diethyloctanediol positional isomers, 1,3-butylene glycol, cyclohexanediol, 1,4-cyclohexanedimethanol, 1,6-hexanediol, 1,2- and 1,4-cyclohexanediol, hydrogenated bisphenol A (2,2-bis(4-hydroxycyclohexyl) propane), 2,2-dimethyl-3-hydroxypropyl (2,2-dimethyl-3-hydroxypropionate).

Examples of suitable triols are trimethylolethane, trimethylolpropane or glycerol. Suitable higher functional alcohols are ditrimethylolpropane, pentaerythritol, dipentaerythritol or sorbitol.

Also suitable are higher molecular weight aliphatic and cycloaliphatic polyols, such as polyester polyols, polyether polyols, polycarbonate polyols, hydroxy-functional acrylic resins, hydroxy-functional polyurethanes, hydroxy-functional epoxy resins or corresponding hybrids (cf. Römpp Lexikon Chemie [Römpp Chemistry Lexicon], pages 465-466, 10$^{th}$ edition 1998, Georg-Thieme-Verlag, Stuttgart).

Polyester polyols suitable for the prepolymer synthesis are linear polyesterdiols, as can be prepared in a known manner from aliphatic, cycloaliphatic or aromatic di- or polycarboxylic acids or their anhydrides, such as, for example, succinic, glutaric, adipic, pimelic, suberic, azelaic, sebacic, nonanedicarboxylic, decanedicarboxylic, terephthalic, isophthalic, o-phthalic, tetrahydrophthalic, hexahydrophthalic or trimellitic acid and acid anhydrides, such as o-phthalic, trimellitic or succinic anhydride or mixtures thereof with polyhydric alcohols, such as, for example, ethanediol, di-, tri- or tetraethylene glycol, 1,2-propanediol, di-, tri-, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, 1,8-octanediol, 1,10-decanediol, 1,12-dodecanediol or mixtures thereof, optionally with the concomitant use of higher functional polyols, such as trimethylolpropane or glycerol. Suitable polyhydric alcohols for the preparation of the polyester polyols are of course also cycloaliphatic and/or aromatic di- and polyhydroxy compounds. Instead of the free polycarboxylic acid, it is also possible to use the corresponding polycarboxylic anhydrides or corresponding polycarboxylic esters of lower alcohols or mixtures thereof for the preparation of the polyesters.

Polyester polyols also suitable for the prepolymer synthesis are homo- or copolymers of lactones, which are preferably obtained by an addition reaction of lactones or lactone mixtures, such as butyrolactone, ε-caprolactone and/or methyl-ε-caprolactone, with suitable difunctional and/or higher functional initiator molecules, such as, for example, the low molecular weight, polyhydric alcohols mentioned above as synthesis components for polyester polyols.

Polycarbonates having hydroxyl groups are also suitable as a polyhydroxy component for the prepolymer synthesis, for example those which can be prepared by reacting diols, such as 1,4-butanediol and/or 1,6-hexanediol and/or 3-methylpentanediol, with diaryl carbonates, e.g. diphenyl carbonate, dimethyl carbonate or phosgene.

Polyether polyols suitable for the prepolymer synthesis are, for example, the polyadducts of styrene oxides, of ethylene oxide, of propylene oxide, tetrahydrofuran, butylene oxide, epichlorohydrin and their mixed adducts and graft products, and the polyether polyols obtained by condensation of polyhydric alcohols or mixtures thereof and the polyether polyols obtained by alkoxylation of polyhydric alcohols, amines and amino alcohols. Preferred polyether polyols are poly(propylene oxides), poly(ethylene oxides) and combinations thereof, in the form of random or block copolymers, or poly(tetrahydrofurans) and mixtures thereof having an OH functionality of 1.5 to 6 and a number average molecular weight of between 200 and 18 000 g/mol, preferably having an OH functionality of 1.8 to 4.0 and a number average molecular weight of 600 to 8000 g/mol and particularly preferably having an OH functionality of 1.9 to 3.1 and a number average molecular weight of 650 to 4500 g/mol.

Suitable amines for the prepolymer synthesis are all oligomeric or polymeric, primary or secondary, di-, tri- or polyfunctional amines. For example, these may be: ethylenediamine, diethylenetriamine, triethylenetetramine, propylenediamine, diaminocyclohexane, diaminobenzene, diaminobisphenyl, triaminobenzene, difunctional, trifunctional and higher functional polyamines, such as, for example, the Jeffamines®, amine-terminated polymers having number average molar masses of 10 000 g/mol or any desired mixtures thereof with one another.

Preferred prepolymers are those based on the abovementioned synthesis components having urethane and/or allophanate groups with number average molecular weights of 200 to 10 000 g/mol, preferably having number average molecular weights of 500 to 8000 g/mol. Particularly preferred prepolymers are allophanates based on HDI or TMDI and di- or trifunctional polyether polyols having number average molar masses of 1000 to 8000 g/mol.

It is, if appropriate, also possible for the isocyanate component a) to contain a proportionate amount of isocyanates which are partly reacted with isocyanate-reactive ethylenically unsaturated compounds. α,β-Unsaturated carboxylic acid derivatives, such as acrylates, methacrylates, maleates, fumarates, maleimides, acrylamides and vinyl ether, propenyl ether, allyl ether and compounds which contain dicyclopentadienyl units and have at least one group reactive toward isocyanates are preferably used here as isocyanate-reactive ethylenically unsaturated compounds. Acrylates and methacrylates having at least one isocyanate-reactive group are particularly preferred. Suitable hydroxy-functional acrylates or methacrylates are, for example, compounds such as 2-hydroxyethyl (meth)acrylate, polyethylene oxide mono(meth)acrylates, polypropylene oxide mono (meth)acrylates, polyalkylene oxide mono(meth)acrylates, poly("epsilon"-caprolactone) mono(meth)acrylates, such as, for example, Tone® M100 (Dow, USA), 2-hydroxypropyl (meth)acrylate, 4-hydroxybutyl (meth)acrylate, 3-hydroxy-2,2-dimethylpropyl (meth)acrylate, the hydroxy-functional mono-, di- or tetra(meth)acrylates of polyhydric alcohols, such as trimethylolpropane, glycerol, pentaerythritol, dipentaerythritol, ethoxylated, propoxylated or alkoxylated trimethylolpropane, glycerol, pentaerythritol, dipentaerythritol or the industrial mixtures thereof. In addition, isocyanate-reactive oligomeric or polymeric unsaturated compounds containing acrylate and/or methacrylate groups, alone or in combination with the abovementioned monomeric compounds, are suitable. The proportion of isocyanates which are partly reacted with isocyanate-reactive ethylenically unsaturated compounds in the isocyanate component a) is 0 to 99%, preferably 0 to 50%, particularly preferably 0 to 25% and very particularly preferably 0 to 15%.

The NCO groups of polyisocyanates of component a) can also be completely partly blocked with the blocking agents customary per se in industry. These are, for example, alcohols, lactams, oximes, malonic esters, alkyl acetoacetates, triazoles, phenols, imidazoles, pyrazoles and amines, such as, for example, butanone oxime, diisopropylamine, 1,2,4-triazole, dimethyl-1,2,4-triazole, imidazole, diethyl malonate, ethyl acetoacetate, acetone oxime, 3,5-dimethyl-pyrazole, epsilon-caprolactam, N-tert-butylbenzylamine, cyclopentanone carboxyethyl ester or any mixtures of these blocking agents.

Polyisocyanates and/or prepolymers of the abovementioned type based on HDI, TMDI and/or TIN are preferably used in component a).

Polyisocyanates based on HDI with isocyanurate and/or iminooxadiazinedione structures are particularly preferably used.

Also particularly preferred is the use of prepolymers preferably having NCO functionalities of 2 to 5, particularly preferably those having primary NCO groups. Examples of such prepolymers are allophanates or urethanes or mixtures thereof, preferably based on HDI and/or TMDI, and polyether- and/or polyester- or polycarbonate polyols.

The abovementioned polyisocyanates or prepolymers preferably have residual contents of free monomeric isocyanate of less than 1% by weight, particularly preferably less than 0.5% by weight, very particularly preferably less than 0.2% by weight.

In principle, all polyfunctional, isocyanate-reactive compounds which have on average at least 1.5 isocyanate-reactive groups per molecule can be used as component b).

Isocyanate-reactive groups in the context of the present invention are preferably hydroxyl, amino or thiol groups, hydroxy compounds being particularly preferred.

Suitable polyfunctional, isocyanate-reactive compounds are, for example, polyester-, polyether-, polycarbonate-, poly(meth)acrylate- and/or polyurethanepolyols.

Suitable polyester polyols are, for example, linear polyesterdiols or branched polyesterdiols as are obtained in a known manner from aliphatic, cycloaliphatic or aromatic di- or polycarboxylic acids or their anhydrides with polyhydric alcohols having an OH functionality ≥2.

Examples of such di- of polycarboxylic acids or anhydrides are succinic, glutaric, adipic, pimelic, suberic, azelaic, sebacic, nonanedicarboxylic, decanedicarboxylic, terephthalic, isophthalic, o-phthalic, tetrahydrophthalic, hexahydrophthalic or trimellitic acid and acid anhydrides, such as o-phthalic, trimellitic or succinic anhydride, or any mixtures thereof with one another.

Examples of such suitable alcohols are ethanediol, di-, tri- or tetraethylene glycol, 1,2-propanediol, di-, tri- or tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, 1,8-octanediol, 1,10-decanediol, 1,12-dodecanediol, trimethylolpropane, glycerol or any mixtures thereof with one another.

The polyester polyols may also be based on natural raw materials, such as castor oil. It is also possible for the polyester polyols to be based on homo- or copolymers of lactones, as can preferably be obtained by an addition reaction of lactones or lactone mixtures, such as butyrolactone, ε-caprolactone and/or methyl-ε-caprolactone, with hydroxy-functional compounds, such as polyhydric alcohols having an OH functionality ≥2, for example of the abovementioned type.

Such polyester polyols preferably have number average molar masses of 400 to 8000 g/mol, particularly preferably of 500 to 4000 g/mol. Their OH functionality is preferably 1.5 to 3.5, particularly preferably 1.8 to 3.0.

Suitable polycarbonate polyols are obtainable in a manner known per se by reacting organic carbonates or phosgene with diols or diol mixtures.

Suitable organic carbonates are dimethyl, diethyl and diphenyl carbonate.

Suitable diols or mixtures comprise the polyhydric alcohols mentioned per se in connection with the polyester segments and having an OH functionality ≥2, preferably 1,4-butanediol, 1,6-hexanediol and/or 3-methylpentanediol, or polyester polyols can be converted into polycarbonate polyols.

Such polycarbonate polyols preferably have number average molar masses of 400 to 4000 g/mol, particularly preferably of 500 to 2400 g/mol. The OH functionality of these polyols is preferably 1.8 to 3.2, particularly preferably 1.9 to 3.0.

Suitable polyether polyols are polyadducts of cyclic ethers with OH- or NH-functional initiator molecules, which polyadducts preferably have a block structure.

Suitable cyclic ethers are, for example, styrene oxides, ethylene oxide, propylene oxide, tetrahydrofuran, butylene oxide, epichlorohydrin and any mixtures thereof.

The polyhydric alcohols mentioned in connection with the polyester polyols and having an OH functionality of ≥2 and primary or secondary amines and amino alcohols can be used as initiators.

Such polyether polyols preferably have number average molar masses of 250 to 10 000 g/mol, particularly preferably of 500 to 8500 g/mol and very particularly preferably of 600 to 4500 g/mol. The OH functionality is preferably 1.5 to 4.0, particularly preferably 1.8 to 3.0.

In addition, aliphatic, araliphatic or cycloaliphatic di-, tri- or polyfunctional alcohols which have a low molecular weight, i.e. have molecular weights of less than 500 g/mol, and a short chain, i.e. contain 2 to 20 carbon atoms, are also suitable as constituents of component b) as polyfunctional, isocyanate-reactive compounds.

These may be, for example, ethylene glycol, diethylene glycol, triethylene glycol, tetraethylene glycol, dipropylene glycol, tripropylene glycol, 1,2-propanediol, 1,3-propanediol, 1,4-butanediol, neopentyl glycol, 2-ethyl-2-butylpropanediol, trimethylpentanediol, diethyloctanediol positional isomers, 1,3-butylene glycol, cyclohexanediol, 1,4-cyclohexanedimethanol, 1,6-hexanediol, 1,2- and 1,4-cyclohexanediol, hydrogenated bisphenol A (2,2-bis(4-hydroxycyclohexyl)propane), 2,2-dimethyl-3-hydroxypropyl 2,2-dimethyl-3-hydroxypropionate. Examples of suitable triols are trimethylolethane, trimethylolpropane or glycerol. Suitable higher functional alcohols are ditrimethylolpropane, pentaerythritol, dipentaerythritol or sorbitol.

Preferred components b) are polyether polyols are poly (propylene oxides), poly(ethylene oxides) and combinations thereof, in the form of random or block copolymers, and block copolymers of propylene oxide and/or ethylene oxide which additionally contain tetrahydrofuran, butylene oxide or ε-caprolactone as monomer units, and mixtures thereof having an OH functionality of 1.5 to 6 and a number average molar mass between 200 and 18 000 g/mol, particularly preferably having an OH functionality of 1.8 to 4.0 and a number average molar mass between 600 and 8000 g/mol and very particularly preferably having an OH functionality of 1.9 to 3.1 and a number average molar mass between 650 and 4500 g/mol.

Combinations of abovementioned isocyanate components a) and isocyanate-reactive components b) which have as high a molecular weight as possible between the corresponding functional groups and/or have as low functionalities as possible are furthermore preferred for the preparation of the matrix A), but the functionalities have to be sufficiently high to be able to produce a three-dimensional network.

Furthermore, those combinations in which the functional groups of the isocyanate-reactive components b) are present in molar excess relative to the functional groups of the isocyanate components a) are also preferred.

Compounds having a vinyl ether, acrylate or methacrylate group, particularly preferably acrylate and/or methacrylate groups, are preferably used in component B).

Compounds having the abovementioned type having a refractive index $n_D^{20}$ f greater than 1.54, preferably of greater than 1.55 and particularly preferably of greater than 1.58 are preferably used in B).

Compounds of the abovementioned type having molecular weights of less than 1500 g/mol, particularly preferably of less than 1000 g/mol, are preferred in B).

Compounds such as α,β-unsaturated carboxylic acid derivatives, such as acrylates, methacrylates, maleates, fumarates, maleimides, acrylamides and furthermore vinyl ether, propenyl ether, allyl ether and compounds containing dicyclopentadienyl units and olefinically unsaturated compounds, such as, for example, styrene, α-methylstyrene, vinyltoluene, olefinins, such as, for example, 1-octene and/or 1-decene, vinyl esters, (meth)acrylonitrile, (meth)acrylamide, methacrylic acid, acrylic acid can be used in component B). Acrylates and methacrylates are preferred.

In general, esters of acrylic acid or methacrylic acid are designated as acrylates or methacrylates, respectively. Examples of acrylates and methacrylates which can be used are methyl acrylate, methyl methacrylate, ethyl acrylate, ethyl methacrylate, ethoxyethyl acrylate, ethoxyethyl methacrylate, n-butyl acrylate, n-butyl methacrylate, tert-butyl acrylate, tert-butyl methacrylate, hexyl acrylate, hexyl methacrylate, 2-ethylhexyl acrylate, 2-ethylhexyl methacrylate, butoxyethyl acrylate, butoxyethyl methacrylate, lauryl acrylate, lauryl methacrylate, isobornyl acrylate, isobornyl methacrylate, phenyl acrylate, phenyl methacrylate, p-chlorophenyl acrylate, p-chlorophenyl methacrylate, p-bromophenyl acrylate, p-bromophenyl methacrylate, 2,4,6-trichlorophenyl acrylate, 2,4,6-trichlorophenyl methacrylate, 2,4,6-tribromophenyl acrylate, 2,4,6-tribromophenyl methacrylate, pentachlorophenyl acrylate, pentachlorophenyl methacrylate, pentabromophenyl acrylate, pentabromophenyl methacrylate, pentabromobenzyl acrylate, pentabromobenzyl methacrylate, phenoxyethyl acrylate, phenoxyethyl methacrylate, phenoxyethoxyethyl acrylate, phenoxyethoxyethyl methacrylate, 2-naphthyl acrylate, 2-naphthyl methacrylate, 1,4-bis(2-thionaphthyl)-2-butyl acrylate, 1,4-bis(2-thionaphthyl)-2-butyl methacrylate, propane-2,2-diylbis[(2,6-dibromo-4,1-phenylene)oxy(2-{[3,3,3-tris(4-chlorophenyl)propanoyl]oxy}propane-3,1-diyl)oxyethane-2,1-diyl] diacrylate, bisphenol A diacrylate, bisphenol A dimethacrylate, tetrabromobisphenol A diacrylate, tetrabromobisphenol A dimethacrylate and the ethoxylated analogue compounds thereof, N-carbazolyl acrylates, to mention but a selection of acrylates and methacrylates which can be used.

Of course, urethane acrylates can also be used as component B). Urethane acrylates are understood as meaning compounds having at least one acrylate group which additionally has at least one urethane bond. It is known that such compounds can be obtained by reacting a hydroxy-functional acrylate with an isocyanate-functional compound.

Examples of isocyanates which can be used for this purpose are aromatic, araliphatic, aliphatic and cycloaliphatic di-, tri- or polyisocyanates. It is also possible to use mixtures of such di-, tri- or polyisocyanates. Examples of suitable di-, tri- or polyisocyanates are butylene diisocyanate, hexamethylene diisocyanate (HDI), isophorone diisocyanate (IPDI), 1,8-diisocyanato-4-(isocyanatomethyl)octane, 2,2,4- and/or 2,4,4-trimethylhexamethylene diisocyanate, the isomeric bis(4,4'-isocyanatocyclohexyl) methanes and mixtures thereof having any isomer content, isocyanatomethyl-1,8-octane diisocyanate, 1,4-cyclohexylene diisocyanate, the isomeric cyclohexanedimethylene diisocyanate, 1,4-phenylene diisocyanate, 2,4- and/or 2,6-toluene diisocyanate, 1,5-naphthylene diisocyanate, 2,4'- or 4,4'-diphenylmethane diisocyanate, 1,5-naphthylene diisocyanate, triphenylmethane 4,4',4''-triisocyanate, and tris(p-isocyanatophenyl) thiophosphate or derivatives thereof having a urethane, urea, carbodiimide, acylurea, isocyanurate, allophanate, biuret, oxadiazinetrione, uretdione or iminooxadiazinedione structure and mixtures thereof. Aromatic or araliphatic di-, tri- or polyisocyanates are preferred.

Suitable hydroxy-functional acrylates or methacrylates for the preparation of urethane acrylates are, for example, compounds such as 2-hydroxyethyl (meth)acrylate, polyethylene oxide mono(meth)acrylates, polypropylene oxide mono(meth)acrylates, polyalkylene oxide mono(meth)-acrylates, poly(ε-caprolactone) mono(meth)acrylates, such as, for example, Tone® M100 (Dow, Schwalbach, Germany), 2-hydroxypropyl (meth)acrylate, 4-hydroxybutyl (meth)acrylate, 3-hydroxy-2,2-dimethylpropyl (meth)acrylate, hydroxypropyl (meth)acrylate, 2-hydroxy-3-phenoxypropyl acrylate, the hydroxy-functional mono-, di- or tetraacrylates of polyhydric alcohols, such as trimethylolpropane, glycerol, pentaerythritol, dipentaerythritol, ethoxylated, propoxylated or alkoxylated trimethylolpropane, glycerol, pentaerythritol, dipentaerythritol or the industrial mixtures thereof. 2-Hydroxyethyl acrylate, hydroxypropyl acrylate, 4-hydroxybutyl acrylate and poly(ε-caprolactone) mono(meth)acrylates are preferred. In addition, are suitable as isocyanate-reactive oligomeric or polymeric unsaturated compounds containing acrylate and/or methacrylate groups, alone or in combination with the abovementioned monomeric compounds. The epoxy (meth) acrylates known per se, containing hydroxyl groups and having OH contents of 20 to 300 mg KOH/g or polyurethane (meth)acrylates containing hydroxyl groups and having OH contents of 20 to 300 mg KOH/g or acrylated polyacrylates having OH contents of 20 to 300 mg KOH/g and mixtures thereof with one another and mixtures with unsaturated polyesters containing hydroxyl groups and mixtures with polyester (meth)acrylates or mixtures of unsaturated polyesters containing hydroxyl groups with polyester (meth) acrylates can likewise be used. Such compounds are also described in P. K. T. Oldring (Ed.), Chemistry & Technology of UV & EB Formulations For Coatings, Inks & Paints, Vol. 2, 1991, SITA Technology, London, pages 37-56. Epoxy acrylates containing hydroxyl groups and having a defined hydroxy functionality are preferred. Epoxy (meth)acrylates containing hydroxyl groups are based in particular on reaction products of acrylic acid and/or methacrylic acid with epoxides (glycidyl compounds) of monomeric, oligomeric or polymeric bisphenol A, bisphenol F, hexanediol and/or butanediol or the ethoxylated and/or propoxylated derivatives thereof. Epoxy acrylates having a defined functionality, as can be obtained from the known reaction of acrylic acid and/or methacrylic acid and glycidyl (meth)acrylate, are furthermore preferred.

In a particularly preferred embodiment of the invention, the writing monomer component B) comprised one or more compounds of the formulae (I) to (III):

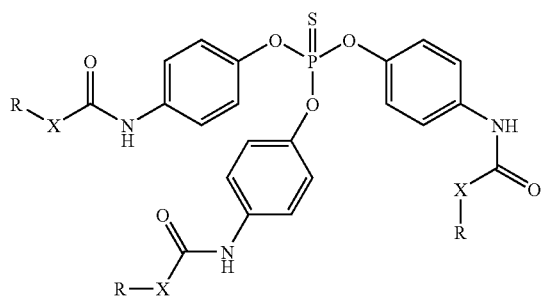

formula (I)

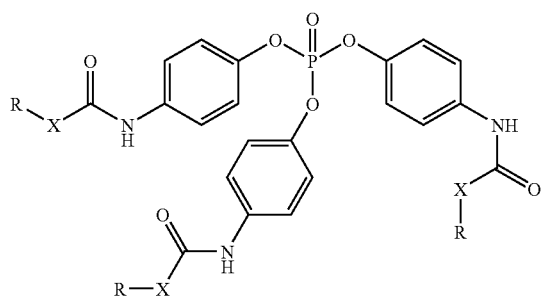

formula (II)

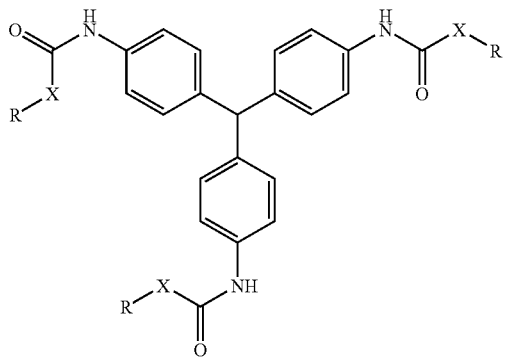

formula (III)

in which
R, independently of one another, is in each case a radiation-curable group and
X independently of one another, is in each case a single bond between R and C=O or a linear, branched or cyclic hydrocarbon radical optionally containing heteroatoms and/or optionally substituted by functional groups.

R is preferably a vinyl ether, acrylate or methacrylate group, particularly preferably an acrylate group.

In principle, one or more of the carbon-bonded hydrogen atoms of the group R can also be replaced by $C_1$- to $C_5$-alkyl groups, which however is not preferred.

The group X preferably has 2 to 40 carbon atoms and one or more oxygen atoms present in the form of ether bridges. X may be either linear or branched or cyclic and substituted by functional groups. Particularly preferably, the group X is in each case a linear or branched oxyalkylene or polyoxyalkylene group.

Preferred polyoxyalkylene groups have up to 10, preferably up to 8, repeating units of the respective oxyalkylene group.

In principle, it is possible for X to have identical or different oxyalkylene groups as repeating units, one such repeating unit preferably having 2 to 6, particularly preferably 2 to 4, carbon atoms. Particularly preferred oxyalkylene units are oxyethylene and in each case the isomeric oxypropylenes or oxybutylenes.

The repeating units within the respective group X may be present completely or partly in a blockwise or random distribution.

In a preferred embodiment of the invention, X independently of one another is in each case an oxyalkylene unit selected from the group consisting of —$CH_2$—$CH_2$—O—, —$CH_2$—$CHCH_3$—O—, —$CHCH_3$—$CH_2$—O—, —O($CH_2$—$CHCH_3$—O)$_n$—, where n is an integer from 2 to 7, and —O—$CH_2$—$CH_2$—(O—($CH_2$)$_5$—CO)$_m$—, where m is an integer from 1 to 5.

One or more photoinitiators are used as component C). These are usually initiators which can be activated by actinic radiation and initiate a polymerization of the corresponding polymerizable groups. Photoinitiators are compounds which are known per se and are sold commercially, a distinction being made between monomolecular (type I) and bimolecular (type II) initiators. Furthermore, depending on the chemical nature, these initiators are used for free radical, anionic (or) cationic (or mixed) forms of the abovementioned polymerizations.

(Type I) systems for free radical photopolymerization are, for example, aromatic ketone compounds, e.g. benzophenones, in combination with tertiary amines, alkylbenzophenones, 4,4'-bis(dimethylamino)benzophenone (Michler's ketone), anthrone and halogenated benzophenones or mixtures of said types. (Type II) initiators, such as benzoin and its derivatives, benzil ketals, acylphosphine oxides, e.g. 2,4,6-trimethylbenzoyldiphenylphosphine oxide, bisacylophosphine oxide, phenylglyoxylic ester, camphorquinone, alpha-aminoalkylphenone, alpha,alpha-dialkoxyacetophenone, 1-[4-(phenylthio)phenyl]octane-1,2-dione 2-(O-benzoyloxime) and alpha-hydroxyalkylphenone are furthermore suitable. The photoinitiator systems described in EP-A 0223587 and consisting of a mixture of an ammonium arylborate and one or more dyes can also be used as a photoinitiator. For example, tetrabutylammonium triphenylhexylborate, tetrabutylammonium tris(3-fluorophenyl)hexylborate and tetrabutylammonium tris(3-chloro-4-methylphenyl)hexylborate are suitable as the ammonium arylborate. Suitable dyes are, for example, new methylene blue, thionine, basic yellow, pinacynol chloride, rhodamine 6G, gallocyanine, ethyl violet, victoria blue R, celestine blue, quinaldine red, crystal violet, brilliant green, astrazon orange G, darrow red, pyronine Y, basic red 29, pyrillium I, cyanine and methylene blue, azure A (Cunningham et al., RadTech '98 North America UV/EB Conference Proceedings, Chicago, Apr. 19-22, 1998).

The photoinitiators used for the anionic polymerization are as a rule (type I) systems and are derived from transition metal complexes of the first row. Chromium salts, such as, for example, trans-Cr($NH_3$)$_2$(NCS)$_4^-$ (Kutal et al, Macromolecules 1991, 24, 6872) or ferrocenyl compounds (Yamaguchi et al. Macromolecules 2000, 33, 1152) are known here. A further possibility of anionic polymerization consists in the use of dyes such as crystal violet leuconitrile or malachite green leuconitrile, which can polymerize cyanoacrylates by photolytic decomposition (Neckers et al., Macromolecules 2000, 33, 7761). However, the chromophore is incorporated into the polymer so that the resulting polymers are coloured throughout.

The photoinitiators used for the cationic polymerization substantially comprise three classes: aryldiazonium salts, onium salts (here specifically: iodonium, sulphonium and selenonium salts) and organometallic compounds. Under irradiation, both in the presence and in the absence of a hydrogen donor, phenyldiazonium salts can produce a cation which initiates the polymerization. The efficiency of the overall system is determined by the nature of the counterion used for the diazonium compound. The slightly reactive but very expensive $SbF_6^-$, $AsF_6^-$ or $PF_6^-$ are preferred here. These compounds are as a rule not very suitable for use in the coating of thin films since the surface quality is reduced by the nitrogen liberated after exposure (pinholes) (Li et al., Polymeric Materials Science and Engineering, 2001, 84, 139). Very widely used and also commercially available in a variety of forms are onium salts, especially sulphonium and iodonium salts. The photochemistry of these compounds has been investigated for a long time. The iodonium salts initially undergo homolytic decomposition after excitation and thus produce a free radical and a radical cation which is stabilized by H abstraction, releases a proton and then initiates the cationic polymerization (Dektar et al. J. Org. Chem. 1990, 55, 639; J. Org. Chem., 1991, 56, 1838). This mechanism permits the use of iodonium salts also for free radical photopolymerization. Once again, the choice of the counterion is of considerable importance here and the very expensive $SbF_6^-$, $AsF_6^-$ or $PF_6^-$ are likewise preferred. Otherwise, the choice of the substitution of the aromatic is quite free in this structure and is determined substantially by the availability of suitable starting building blocks for the synthesis. The sulphonium salts are compounds which decompose according to Norrish(II) (Crivello et al., Macromolecules, 2000, 33, 825). In the case of the sulphonium salts, too, the choice of the counterion is of critical importance, which manifests itself substantially in the curing rate of the polymers. The best results are obtained as a rule with $SbF_6^-$ salts. Since the self-absorption of iodonium and sulphonium salts is at <300 nm, these compounds must be appropriately sensitized for the photopolymerization with near UV or short-wave visible light. This is achieved by the use of relatively highly absorbing aromatics, such as, for example, anthracene and derivatives (Gu et al., Am. Chem. Soc. Polymer Preprints, 2000, 41 (2), 1266) or phenothiazine or derivatives thereof (Hua et al, Macromolecules 2001, 34, 2488-2494).

It may also be advantageous to use mixtures of these compounds. Depending on the radiation source used for curing, type and concentration of photoinitiator must be adapted in the manner known to the person skilled in the art. The abovementioned configuration with regard to the photopolymerization is easily possible for a person skilled in the art in the form of routine experiments within the belowmentioned quantity ranges of the components and the synthesis components available in each case for selection, in particular the preferred synthesis components.

Preferred photoinitiators C) are mixtures of tetrabutylammonium tetrahexylborate, tetrabutylammonium triphenylhexylborate, tetrabutylammonium tris(3-fluorophenyl)hexylborate and tetrabutylammonium tris(3-chloro-4-methylphenyl)hexylborate with dyes, such as, for example, astrazon orange G, methylene blue, new methylene blue, azure A, pyrillium I, safranine O, cyanine, gallocyanine, brilliant green, crystal violet, ethyl violet and thionine.

Furthermore, the formulations according to the invention may also be used with free radical stabilizers, catalysts and further additives in addition to the components A) to C).

Suitable free radical stabilizers are inhibitors and antioxidants, as described in "Methoden der organischen Chemie [Methods of Organic Chemistry]" (Houben-Weyl), 4$^{th}$ edition, volume XIV/1, page 433 et seq., Georg Thieme Verlag, Stuttgart 1961. Suitable classes of substances are, for example, phenols, such as, for example, 2,6-di-tert-butyl-4-methylphenol, cresols, hydroquinones, benzyl alcohols, such as, for example, benzhydrol, optionally also quinones, such as, for example, 2,5-di-tert-butylquinone, optionally also aromatic amines, such as diisopropylamine or phenothiazine. Preferred free radical stabilizers are 2,6-di-tert-butyl-4-methylphenol, phenothiazine and benzhydrol.

Furthermore, one or more catalysts may be used. These preferably catalyse the urethane formation. Amines and metal compounds of the metals tin, zinc, iron, bismuth, molybdenum, cobalt, calcium, magnesium and zirconium are preferably suitable for this purpose. Tin octanoate, zinc octanoate, dibutyltin dilaurate, dimethyltin dicarboxylate, iron(III) acetylacetonate, iron(II) chloride, zinc chloride, tetraalkylammonium hydroxides, alkali metal hydroxides, alkali metal alcoholates, alkali metal salts of long-chain fatty acids having 10 to 20 carbon atoms and optionally OH side groups, lead octanoate and tertiary amines, such as triethylamine, tributylamine, dimethylbenzylamine, dicyclohexylmethylamine, dimethylcyclohexylamine, N,N,N',N'-tetramethyldiaminodiethyl ether, bis(dimethylaminopropyl) urea, N-methyl- or N-ethylmorpholine, N,N'-dimorpholinodiethyl ether (DMDEE), N-cyclohexylmorpholine, N,N,N',N'-tetramethylethylenediamine, N,N,N',N'-tetramethylbutanediamine, N,N,N',N'-tetramethyl-1,6-hexanediamine, pentamethyldiethylenetriamine, dimethylpiperazine, N-dimethylaminoethylpiperidine, 1,2-dimethylimidazole, N-hydroxypropylimidazole, 1-azabicyclo[2.2.0]octane, 1,4-diazabicyclo[2.2.2]octane (Dabco) or alkanolamine compounds, such as triethanolamine, triisopropanolamine, N-methyl- and N-ethyldiethanolamine, dimethylaminoethanol, 2-(N,N-dimethylaminoethoxy)ethanol or N-tris(diallylaminoalkyl)hexahydrotriazines, e.g. N,N',N'-tris(dimethylaminopropyl)-s-hexahydrotriazine, 1,4-diazabicyclo[2.2.2]octane, diazabicyclononane, diazabicycloundecane, 1,1,3,3-tetramethylguanidine, 1,3,4,6,7,8-hexahydro-1-methyl-2H-pyrimido(1,2-a)pyrimidine are particularly preferred.

Particularly preferred catalysts are dibutyltin dilaurate, dimethyltin dicarboxylate, iron(III) acetylacetonate, 1,4-diazabicyclo[2.2.2]octane, diazabicyclononane, diazabicycloundecane, 1,1,3,3-tetramethylguanidine, 1,3,4,6,7,8-hexahydro-1-methyl-2H-pyrimido(1,2-a)pyrimidine.

For example, solvents, plasticizers, levelling agents, wetting agents, antifoams or adhesion promoters, but also polyurethanes, thermoplastic polymers, oligomers, compounds having further functional groups, such as, for example, acetals, epoxide, oxetanes, oxazolines, dioxolanes and/or hydrophilic groups, such as, for example, salts and/or polyethylene oxides may be present as further auxiliaries and additives.

Readily volatile solvents having good compatibility with the formulations according to the invention, for example ethyl acetate, butyl acetate, acetone, are preferably used as solvents.

Liquids having good dissolution properties, low volatility and high boiling point are preferably used as plasticizers; for example, these may be diisobutyl adipate, di-n-butyl adipate, dibutyl phthalate, non-hydroxy-functional polyethers, such as, for example, polyethylene glycol dimethyl ether having a number average molar mass of 250 g/mol to 2000 g/mol or polypropylene glycol dimethyl ether or mixtures of said compounds.

It may also be advantageous simultaneously to use a plurality of additives of one type. Of course, it may also be advantageous to use a plurality of additives of a plurality of types.

Layers, layer structures and muldings obtainable from formulations which contain the photopolymer formulations according to the invention furthermore typically have $\Delta n$ values greater than 0.010, preferably greater than 0.014, particularly preferably greater than 0.017, very particularly preferably greater than 0.020.

The photopolymer formulations according to the invention are therefore outstandingly suitable for the production of holographic media and holographic photopolymer films.

The present invention therefore furthermore relates to the use of the media according to the invention for recording visual holograms and for producing optical elements, images or representations.

The invention therefore also relates to a method for exposing the media according to the invention, in which writing monomers are selectively polymerized by actinic radiation.

After appropriate holographic exposure, such holographic media are suitable for the production of holographic optical elements which have, for example, the function of an optical lens, of a mirror, of a deflecting mirror, of a filter, of a diffusion screen, of a diffraction element, of a light guide, of a waveguide, of a projection screen and/or of a mask.

In addition, holographic images or representations can also be produced therewith, such as, for example, for personal portraits, biometric representations in security documents or generally images or image structures for advertising, security labels, trademark protection, trademark branding, labels, design elements, decorations, illustrations, multijourney tickets, images and the like and images which can represent digital data, inter alia also in combination with the products described above.

All the references described above are incorporated by reference in its entirety for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

Unless noted otherwise, all stated percentages are based on percent by weight.

Measurement of the Refractive Indices of the Photopolymerizable Monomers

The refractive index n as a function of the wavelength of the samples were obtained from the transmission and reflection spectra. For this purpose, about 100-300 nm thick films of the samples were applied to quartz glass supports from dilute solution in butyl acetate by spincoating. The transmission and reflection spectrum of this layer packet was measured using a spectrometer from STEAG ETA-Optik, CD measurement system ETA-RT, and the layer thickness and the spectral curve of n were then adapted to the measured transmission and reflection spectra. This is effected using the internal software of the spectrometer and additionally requires the refractive index data of the quartz glass substrate, which were determined in a blank measurement beforehand. The refractive index $n_{Mo}$ relates to the wavelength of a sodium vapour lamp of 589 nm and thus corresponds to $n_D^{20}$.

Measurement of the Refractive Indices of the Matrix, Based on a Polymeric Urethane Network For the production of the photopolymer matrices for determining the refractive index $n_{Ma}$, the isocyanate-reactive component b) is, if appropriate, heated to 60° C. Thereafter, the isocyanate component a) is added and mixed in the Speedmixer (from Hauschild) for 1 minute. Subsequently, a solution of component c) is added and is mixed in the Speedmixer again for 1 minute. The solution of component c) is 10 percent by weight in n-ethylpyrrolidone. The correspondingly used amounts of solution can be found in Table 1. The still liquid formulation is applied in the desired thickness to glass plates by knifecoating.

The matrix based on a polymeric network was prepared as a layer about 500 µm to 1000 µm thick on a glass support. The refractive index $n_{ma}$ at the wavelength of the sodium vapour lamp of 589 nm was determined for this sample by means of an Abbe refractometer analogously to DIN 51423-2 and thus corresponds to $n_D^{20}$.

Measurement of the Holographic Properties DE and Δn of the Holographic Media by Means of Two-Beam Interference in the Reflection Arrangement The media produced as described in the section "Production of the holographic media based on photopolymer formulation with photoinitiator for determining the performance parameters E and Δn" were then tested for their holographic properties by means of a measuring arrangement according to FIG. 1, as follows:

The beam of an He—Ne laser (emission wavelength 633 nm) was converted into a parallel homogeneous beam with the aid of a spatial filter (SF) and together with the collimation lens (CL). The final cross sections of the signal and reference beam are fixed by the iris diaphragms (I). The diameter of the iris diaphragm opening is 0.4 cm. The polarization-dependent beam splitters (PBS) split the laser beam into two coherent equally polarized beams. Via the λ/2 plates, the power of the reference beam was adjusted to 0.5 mW and the power of the signal beam to 0.65 mW. The powers were determined using the semiconductor detectors (D) with the sample removed. The angle of incidence (α) of the reference beam is 21.8° and the angle of incidence (β) of the signal beam is 41.8°. At the location of the sample (medium), the interference field of the two overlapping beams produced a grating of light and dark strips which are perpendicular to the angle bisector of the two beams incident on the sample (reflection hologram). The strip spacing Λ, also referred to as grating period, in the medium is ~225 nm (the refractive index of the medium is assumed to be ~1.504).

FIG. 1 shows the holographic experimental setup with which the diffraction efficiency (DE) of the media was measured. FIG. 1 shows the geometry of an HMT at λ=633 nm (He—Ne laser): M=mirror, S=shutter, SF=spatial filter, CL=collimator lens, λ/2=λ/2 plate, PBS=polarization-sensitive beam splitter, D=detector, I=iris diaphragm, α=21.8°, β=41.8° are the angles of incidence of the coherent beams measured outside the sample (the medium).

Holograms were written into the medium in the following manner:

Both shutters (S) are opened for the exposure time t.

Thereafter, with shutters (S) closed, the medium was allowed 5 minutes time for the diffusion of the still unpolymerized writing monomers.

The holograms written were now read in the following manner. The shutter of the signal beam remained closed. The shutter of the reference beam was opened. The iris diaphragm of the reference beam was closed to a diameter of <1 mm. This ensured that, for all angles of rotation (n) of the medium, the beam was always completely in the hologram written beforehand. The turn table then passed, under computer control, through the angular range of from Ω=0° to Ω=20°, with an angle increment of 0.05°. At each angle Ω approached, the powers of the beam transmitted in the zeroth order were measured by means of the corresponding detector D and the powers of the beam diffracted in the first order were measured by means of the detector D. The diffraction efficiency was obtained at each angle Ω approached as the quotient of:

$$\eta = \frac{P_D}{P_D + P_T}$$

$P_D$ is the power in the detector of the diffracted beam and $P_T$ is the power in the detector of the transmitted beam.

By means of the method described above, the Bragg curve, which describes the diffraction efficiency η as a function of the angle of rotation Ω of the hologram written was measured and was stored in a computer. In addition, the intensity transmitted in the zeroth order was also plotted against the angle of rotation Ω and stored in a computer.

The maximum diffraction efficiency (DE=$\eta_{max}$) of the hologram, i.e. its peak value, was determined. For this purpose, the position of the detector of the diffracted beam may have had to be changed in order to determine this maximum value.

The diffractive index contrast Δn and the thickness d of the photopolymer layer were now determined by means of the coupled wave theory (cf.: H. Kogelnik, The Bell System Technical Journal, Volume 48, November 1969, Number 9, page 2909-page 2947) from the measured Bragg curve and the angle variation of the transmitted intensity. The method is described below:

For the Bragg curve η(Ω) of a reflection hologram, the following is true according to Kogelnik:

$$\eta = \frac{1}{1 + \frac{1-(\chi/\Phi)^2}{\sinh^2(\sqrt{\Phi^2 - \chi^2})}}$$

where:

$$\Phi = \frac{\pi \cdot \Delta n \cdot d}{\lambda \cdot \sqrt{\cos(\alpha') \cdot \cos(\alpha' - 2\psi)}}$$

$$\chi = \Delta\theta \cdot \frac{2\pi \cdot \sin(\alpha' - \psi)}{\Lambda \cdot \cos(\alpha' - 2\psi)} \cdot \frac{d}{2}$$

$$\psi = \frac{\beta' - \alpha'}{2}$$

$$\Lambda = \frac{\lambda}{2 \cdot n \cdot \cos(\psi - \alpha')}$$

$$n \cdot \sin(\alpha') = \sin(\alpha), \; n \cdot \sin(\beta') = \sin(\beta)$$

$$\Delta\theta = -\Delta\Omega \cdot \sqrt{\frac{1 - \sin^2(\alpha)}{n^2 - \sin^2(\alpha)}}$$

Φ is the grating strength, χ is the detuning parameter and ψ is the tilt angle of the refractive index grating which was written, α' and β' correspond to the angles α and β on writing the hologram, but measured in the medium. Δθ is the angle detuning measured in the medium, i.e. the deviation from the angle α'. ΔΩ is the angle detuning measured outside the medium, i.e. the deviation from the angle α. n is the mean refractive index of the photopolymer and was set at 1.504. λ is the wavelength of the laser light in a vacuum.

For $\chi=0$, i.e. $\Delta\Omega=0$, the maximum diffraction efficiency (DE=$\eta_{max}$) is then:

$$DE = \tanh^2(\Phi) = \tanh^2\left(\frac{\pi \cdot \Delta n \cdot d}{\lambda \cdot \sqrt{\cos(\alpha') \cdot \cos(\alpha' - 2\psi)}}\right)$$

Figure 2:
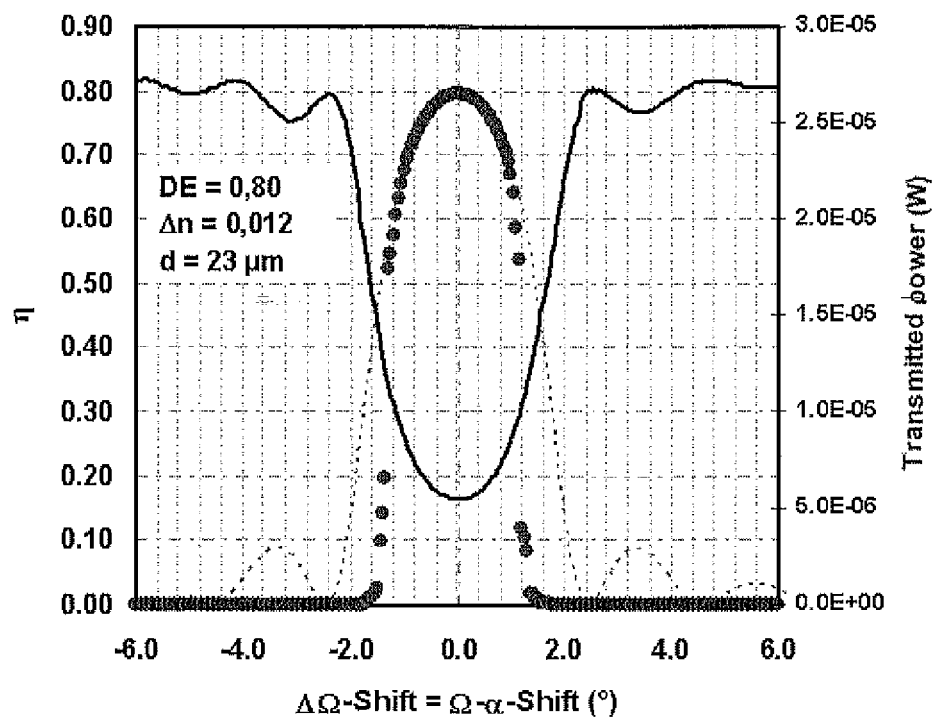
FIG. 2 depicts the plot of the Bragg curve η according to Kogelnik (dashed line), of the measured diffraction efficiency (solid circles) and of the transmitted power (black solid line) against the angle detuning ΔΩ.

The measured data of the diffraction efficiency, the theoretical Bragg curve and the transmitted intensity are, as shown in FIG. 2, plotted against the centred angle of rotation $\Omega-\alpha$ shift. Since, owing to geometric shrinkage and the change in the mean refractive index during the photopolymerization, the angle at which DE is measured deviates from $\alpha$, the x axis is centred about the shift. The shift is typically 0° to 2°.

Since DE is known, the shape of the theoretical Bragg curve according to Kogelnik is determined only by the thickness d of the photopolymer layer. An is subsequently corrected via DE for a given thickness d so that measurement and theory of DE always agree. d is now adapted until the angular positions of the first secondary minima of the theoretical Bragg curve correspond to the angular positions of the first secondary maxima of the transmitted intensity and additionally the full width at half maximum (FWHM) for theoretical Bragg curve and the transmitted intensity correspond.

Since the direction in which a reflection hologram corotates on reconstruction by means of an $\Omega$ scan but the detector for the diffracted light can only cover a finite angular range, the Bragg curve of broad holograms (small d) is not completely covered in an $\Omega$ scan but only the central region in the case of suitable detector positioning. That shape of the transmitted intensity which is complementary to the Bragg curve is therefore additionally used for adapting the layer thickness d.

FIG. 2 shows the plot of the Bragg curve η according to Kogelnik (dashed line), of the measured diffraction efficiency (solid circles) and of the transmitted power (black solid line) against the angle detuning $\Delta\Omega$. Since, owing to geometric shrinkage and the change in the mean refractive index during the photopolymerization, the angle at which DE is measured deviates from $\alpha$, the x axis is centred about the shift. The shift is typically 0° to 2°.

For a formulation, this procedure was possibly repeated several times for different exposure times t on various media in order to determine the mean energy dose of the incident laser beam during writing of the hologram at which DE achieves the saturation value. The mean energy dose E is obtained as follows from the powers of the two part-beams coordinated with the angles α and β ($P_\alpha$=0.50 mW and $P_\beta$=0.67 mW), the exposure time t and the diameter of the iris diaphragm (0.4 cm):

$$E(mJ/cm^2) = \frac{2[P_\alpha + P_\beta] \cdot t(s)}{\pi \cdot 0.4^2 \; cm^2}$$

The powers of the part-beams were adapted so that the same power density is achieved in the medium at the angles α and β used.

Alternatively, a test equivalent to the setup shown in FIG. 1 was also carried out using a green laser with the emission wavelength λ of 532 nm in a vacuum. There, α is 11.5° and β is 33.5° and $P_\alpha$ is 2.00 mW and $P_\beta$ is 2.00 mW.

Measurement of the Plateau Modulus $G_0$ of the Photopolymers by Means of an Oscillation Rheometer in the Present Invention For the preparation of the photopolymer formulation for determining the plateau modulus $G_0$, component B) and optionally additives are dissolved in the isocyanate-reactive component b), optionally at 60° C. Heating is optionally effected to 60° C. for not more than 10 minutes in a drying oven. Thereafter, isocyanate component a) is added and mixed in the Speedmixer for 1 minute. Subsequently, a solution of component c) in butyl acetate is added and is mixed in the Speedmixer again for 1 minute. The concentration of component c) in butyl acetate is 10% by weight. The amounts of this solution which are described in Table 2 were used.

The still liquid formulation is then introduced into the plate-plate measuring system of a rheometer (from Anton Paar Physica, model MCR 301) equipped with the oven model CTD 450 which was preheated to 50° C.). The curing of the matrix of the photopolymer formulation over time is then measured under the following conditions:

Plate spacing 250 μm.

Oscillation measuring mode at a constant circular frequency $\omega_0$ of 10 rad/s and a regulated deformation amplitude of 1%.

Temperature 50° C., normal force regulation to 0 Newton set

Recording of the storage modulus G' over the measuring time for at least 2 hours or until a constant value $G_{max}$ of G' was reached.

A frequency sweep was then carried out on the photopolymer formulation in order to ensure that a plateau modulus $G_0$ characteristic for a polymeric network was reached. The following conditions were chosen:

Oscillation measuring mode over a circular frequency range of 0.5 rad/s<ω<300 rad/s and a regulated deformation amplitude of 1%.

Temperature 50° C., normal force regulation to 0 Newton set

Recording of the storage modulus G' over the circular frequency ω.

If G' varies by less than 30%, based on the maximum value, within the stated circular frequency range, $G_{max}$ is conceived as the plateau modulus $G_0$ to be determined. Examples of typical measured curves are to be found in FIG. 3.

Figure 3:
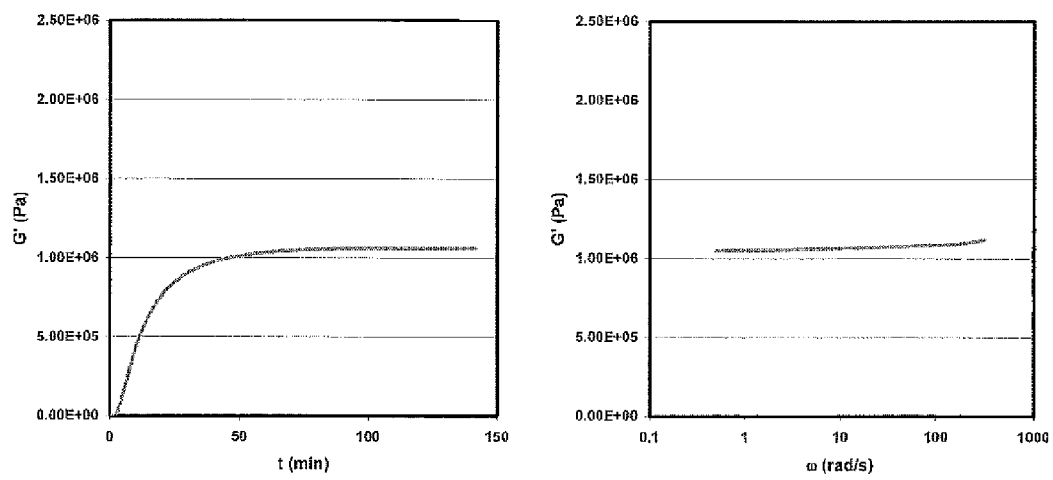
FIG. 3 depicts the curve for the curing of the matrix network (link) and testing for plateau behaviour (G' independent of ω) (right).

FIG. 3 shows the curve for the curing of the matrix network (link) and testing for plateau behaviour (G' independent of ω) (right).

The plateau modulus $G_0$ can be related to the average molecular weight $M_C$ of the segments bridging two polymer strands as follows according to (M. Doi, S. F. Edwards, The Theory of Polymer Dynamics, Oxford Science Publications, 1986).

$$G_0 = \frac{\rho \cdot R \cdot T}{M_C}$$

R is the Avogadro constant, T is the absolute temperature in Kelvin and $\rho$ is the mass density, which for the sake of simplicity was always set at 1 g/cm³. A small plateau modulus $G_0$ or a large average molecular weight $M_C$ of the segments bridging two polymer strands characterize a network having a low crosslinking density.

Isocyanates Used (Components a)

Desmodur® XP 2410 is an experimental product of Bayer MaterialScience AG, Leverkusen, Germany, hexane diisocyanate-based polyisocyanate, proportion of iminooxadiazinedione at least 30%, NCO content: 23.5% (component a1)

Desmodur® XP 2580 is an experimental product of Bayer MaterialScience AG, Leverkusen, Germany, aliphatic polyisocyanate based on hexane diisocyanate, NCO content about 20% (component a2)

Desmodur® XP 2599 is an experimental product of Bayer MaterialScience AG, Leverkusen, Germany, full allophanate of hexane diisocyanate based on Acclaim 4200, NCO content: 5.6-6.4% (component a3)

Preparation of Component 4a)

Component 4a) is an experimental product of Bayer MaterialScience AG, Leverkusen, Germany, urethane of hexane diisocyanate and Acclaim 4200, NCO content: 18.5%.

315.0 g of hexamethylene diisocyanate (HDI) were initially introduced into a round-bottomed flask with stirring and bubbling through of $N_2$, and 0.016 g of isophthaloyl dichloride and 2 drops (about 0.040 g) of dibutyltin dilaurate were added. The mixture was heated to 100° C. and 478.68 g of Acclaim 4200 (polypropylene oxide having a number average molar mass of 4000 g/mol) were added over 75 minutes. Stirring was continued until an NCO value of 18.5% NCO was reached. The reaction is then stopped by cooling to room temperature. The excess HDI is then separated off by distillation via a thin-film evaporator at 140° C. (residue of HDI<0.1%). The product is obtained as a colourless liquid. It has allophanate structures in parts and an average functionality of about 2.6.

Isocyanate-Reactive Components Used (Component B)

Preparation of Polyol b1:

Polyol b1 is an experimental product of Bayer MaterialScience AG, Leverkusen, Germany, block copolymer of Terathane® 650 and ϵ-caprolactone.

0.25 g of zinc octanoate, 172.29 g of ϵ-caprolactone and 27.46 g of a difunctional polytetrahydrofuran polyether polyol (equivalent weight 325 g/mol OH) were initially introduced into a 1 l flask and heated to 150° C. and kept at this temperature until the solids content (proportion of non-volatile constituents) was 99.5% by weight or higher. Thereafter, cooling was effected and the product was obtained as a viscous liquid.

Preparation of Polyol b2:

Polyol b2 is an experimental product of Bayer MaterialScience AG, Leverkusen, Germany, block copolymer of Terathane® 1000 and ϵ-caprolactone.

0.18 g of zinc octanoate, 374.8 g of ϵ-caprolactone and 374.8 g of a difunctional polytetrahydrofuran polyether polyol (equivalent weight 500 g/mol OH) were initially introduced into a 1 l flask and heated to 120° C. and kept at this temperature until the solids content (proportion of non-volatile constituents) was 99.5% by weight or higher. Thereafter, cooling was effected and the product was obtained as a waxy solid.

Polyol b3 is a polypropylene oxide having a number average molar mass of 4000 g/mol, which is sold under the tradename Acclaim® 4200 by Bayer MaterialScience, Leverkusen, Germany.

Polyol b4 is a difunctional copolyether of ethylene oxide and propylene oxide comprising altogether a 50% proportion of ethylene oxide and having an equivalent weight of 984.2 g/mol.

Preparation of Polyol b5:

3.621 kg of Terathane® 1000 were weighed into a 20 l reaction tank equipped with a stirrer, and 525 mg of DMC catalyst were added. Heating was then effected to 105° C. with stirring at about 70 rpm. Air was exchanged for nitrogen by applying a vacuum and eliminating the vacuum with nitrogen three times. After the stirrer speed had been increased to 300 rpm, nitrogen was passed through the mixture from below for 54 minutes with the vacuum pump running, at a pressure of about 0.1 bar. Thereafter, a pressure of 0.2 bar was established by means of nitrogen and 363 g of propylene oxide (PO) were introduced for initiating the polymerization. The pressure increased to 2.42 bar thereby. After 7 minutes, the pressure had decreased to 0.34 bar again and a further 11.379 kg of PO were metered in over a period of 2 h 29 min. at 2.9 bar. 47 minutes after the end of the PO metering, a vacuum was applied at a residual pressure of 1.9 bar and complete degassing was effected. The product was stabilized by addition of 7.5 g of Irganox 1076 and was obtained as a colourless, viscous liquid (OH number: 27.6 mg KOH/g, viscosity at 25° C.: 1498 mPas).

The starting material DMC catalyst is a double metal cyanide catalyst based on zinc hexacyanocobaltate (III), obtainable by the process described in EP-A 700 949

Catalyst Used (Component c)

Fomrez® UL28: urethanization catalyst, dimethylbis[(1-oxoneodecl)oxy]stannane, commercial product of Momentive Performance Chemicals, Wilton, Conn., USA (used as a 10% strength solution in N-ethylpyrrolidone) (component c1).

Radiation-Curing Groups Used (Component B)

Component B1): ethoxylated (3) bisphenol A diacrylates

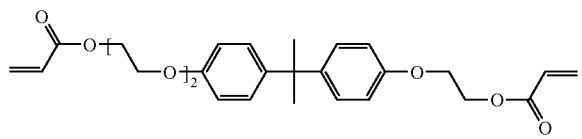

Sartomer Company, 502 Thomas Jones Way Exton, Pa. 19341 (USA).

The refractive index $n_D^{20} = n_{Mo}$ is 1.543 (information in the manufacturer's datasheet).

Component B2): Propane-2,2-diyibis[(2,6-dibromo-4,1-phenylene)oxy(2-{[3,3,3-tris(4-chlorophenyl)propanoyl]oxy}propane-3,1-diyl)oxyethane-2,1-diyl] diacrylate

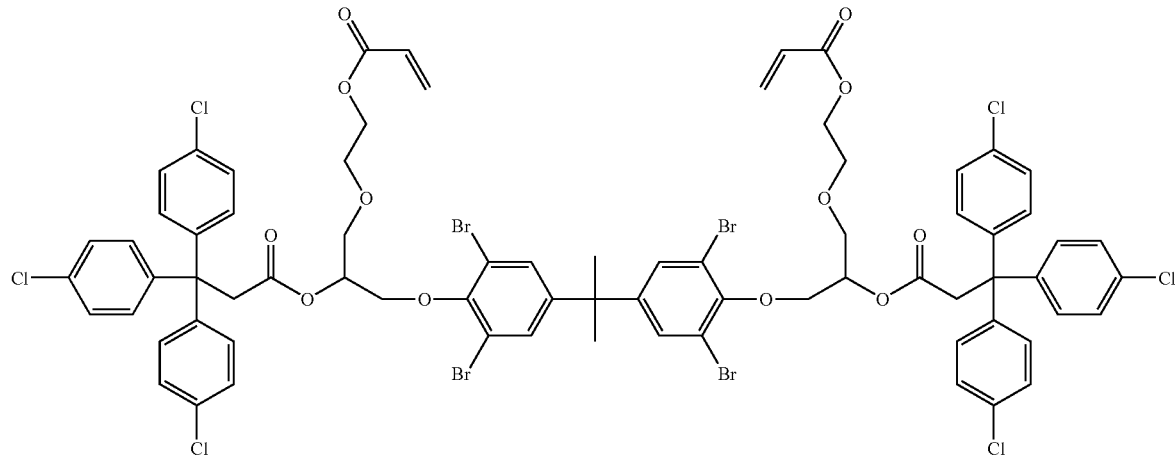 [SMILES: C=CC(=O)OCCOCC(COc1c(Br)cc(C(C)(C)c2cc(Br)c(OCC(COCCOC(=O)C=C)OC(=O)CC(c3ccc(Cl)cc3)(c3ccc(Cl)cc3)c3ccc(Cl)cc3)c(Br)c2)cc1Br)OC(=O)CC(c1ccc(Cl)cc1)(c1ccc(Cl)cc1)c1ccc(Cl)cc1]

Precursor V1 for Component B2)

215.3 g of tetrabromobisphenol A diglycidyl ether (D.E.R. 542, from Dow Chemicals, USA) and 1.1 kg of hydroxyethyl acrylate in 1.5 l of toluene were initially introduced into a 6 l flask having a reflux condenser. 1.06 g of boron trifluoride-diethyl ether complex were added dropwise to this solution at room temperature and stirring was effected for a further 24 h at room temperature. Thereafter, dilution was effected with 1.3 kg of toluene and hydrolysis with 9 g of sodium bicarbonate in 2.5 kg of water. The organic phase separated off was washed three times with 2.5 kg of water and tested for hydroxyethyl acrylate by means of GC. The organic phase was dried using magnesium sulphate. Thereafter, the solvent was distilled off at 5 mbar and cooling was effected.

140.2 g of the precursor V1 in 1.5 kg of tert-butyl methyl ether were initially introduced into a 6 l flask having a reflux condenser and dissolved at room temperature. 136.8 g of 3,3,3-tris(4-chlorophenyl)propionic acid, 3.67 g of dimethylaminopyridine and 69.3 g of dicyclohexylcarbodiimide were added. After a short time, a slightly exothermic reaction began with simultaneous precipitation. Stirring was continued for 1 h at RT. Filtration was effected and the residue was washed twice with 875 ml of 0.2 mol/M aqueous hydrochloric acid each time. The filtrate was then stirred for 30 min. with 875 ml of saturated NaCl solution and then separated in a separating funnel. The organic phase was washed four times with 875 ml of saturated NaCl solution and then dried using magnesium sulphate. 0.88 g of 2,6-di-tert-butyl-4-methylphenol (KB) was added to the residue. Thereafter, the solvent was distilled off at 5 mbar and cooling was effected, and boiling with 2.6 l of isopropanol and cooling were effected three times. The residue obtained was taken up in 1.3 l of tert-butyl methyl ether, kieselguhr was added, filtration was effected and the solvent was dissolved off at 5 mbar and cooling was effected.

The refractive index $n_{Mo}$ is 1.603.

Component B3): Phosphorothioyltris(oxy-4,1-phenyleneiminocarbonyloxyethane-2,1-diyl) triacrylate

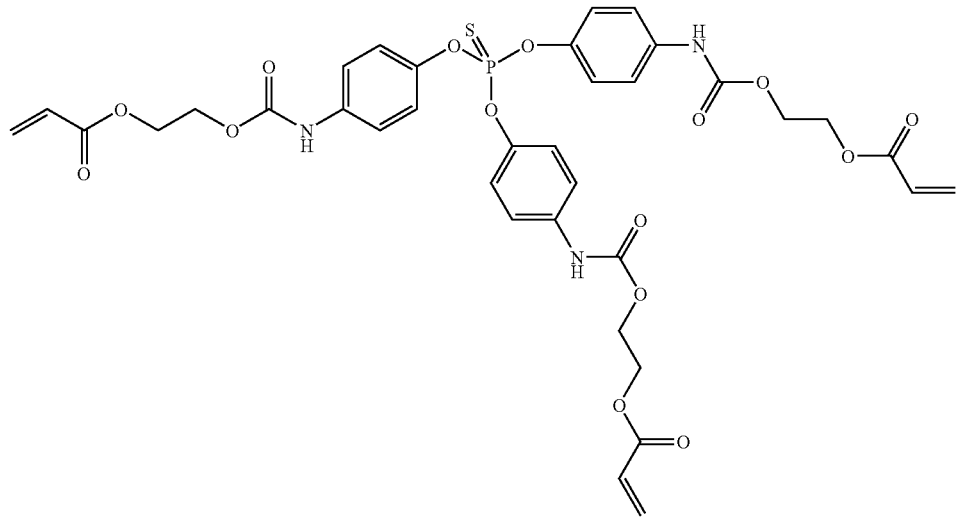 [SMILES: C=CC(=O)OCCOC(=O)Nc1ccc(OP(=S)(Oc2ccc(NC(=O)OCCOC(=O)C=C)cc2)Oc2ccc(NC(=O)OCCOC(=O)C=C)cc2)cc1]

0.1 g of 2,6-di-tert-butyl-4-methylphenol, 213.07 g of a 27% strength solution of tris(p-isocyanatophenyl) thiophosphate in ethyl acetate (Desmodur RFE, product of Bayer MaterialScience AG) were initially introduced into a 500 ml round-bottomed flask and heated to 60° C. Thereafter, 42.37 g of 2-hydroxyethyl acrylate were added dropwise and the mixture was kept further at 60° C. until the isocyanate content had fallen below 0.1%. Thereafter, cooling was effected and the ethyl acetate was completely removed in vacuo. The product is obtained as a semicrystalline solid.

The refractive index $n_{Mo}$ is 1.579.

Component B4): 2-({[3-(methylsulphanyl)phenyl]carbamoyl}oxy)ethyl prop-2-enoate

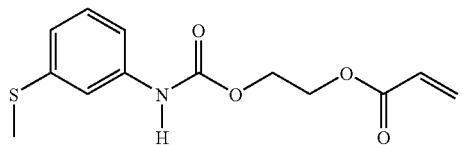 [SMILES: C=CC(=O)OCCOC(=O)Nc1cccc(SC)c1]

0.02 g of 2,6-di-tert-butyl-4-methylphenol, 0.01 g of Desmorapid Z, 11.7 g of 3-(methylthio)phenyl isocyanate were initially introduced into a 100 ml round-bottomed flask and heated to 60° C. Thereafter, 8.2 g of 2-hydroxyethyl acrylate were added dropwise and the mixture was kept further at 60° C. until the isocyanate content had fallen below 0.1%. Cooling was then effected. The product was obtained as a light yellow liquid.

The refractive index $n_{Mo}$ is 1.576.

Photoinitiator Systems Used (Component C)

Description of the System New Methylene Blue+CGI (component C1))

0.1 g of New Methylene Blue, 1.00 g of CGI 909 (experimental product of Ciba Inc., Basel, Switzerland) are dissolved in 3.50 g of n-ethylpyrrolidone in a beaker in the dark or under suitable lighting. The corresponding percentages by weight of this solution (cf. Table 3) are used for producing the example media.

Description of the System Safranine O+CGI (Component C2))

0.1 g of Safranine O, 1.00 g of CGI 909 (experimental product of Ciba Inc., Basel, Switzerland) are dissolved in 3.50 g of n-ethylpyrrolidone in a beaker in the dark or under suitable lighting. The corresponding percentages by weight of this solution (cf. Table 3) are used for producing the example media.

The following three-dimensionally crosslinked polymers as matrix component A) of the photopolymer formulation for determining the refractive index $n_{Ma}$ were prepared by the process described above.

Table 1 describes the exact compositions.

TABLE 1

Matrix components A) for determining the refractive index $n_{Ma}$ at 589 nm.
NCO:OH designates the ratio of the number of equivalents of the functional groups in the components a) and b) in the respective component A)

| Matrix | Isocyanate component | Proportion (gr) | Isocyanate-reactive component | Proportion (gr) | NCO:OH | Catalyst in solution | Proportion (gr) | $n_{Ma}$ |
|---|---|---|---|---|---|---|---|---|
| A1 | a1 | 26.8 | b1 | 72.8 | 1.02:1 | c1 | 0.4 | 1.485 |
| A2 | a1 | 15.4 | b2 | 84.2 | 1.02:1 | c1 | 0.4 | 1.478 |
| A3 | a2 | 2.7 | b4 | 12.3 | 1.02:1 | c1 | 0.018 | 1.470 |
| A4 | a2 | 9.6 | b5 | 90.0 | 1.02:1 | c1 | 0.4 | 1.460 |
| A5 | a3 | 26.6 | b3 | 73.0 | 1.02:1 | c1 | 0.4 | 1.455 |
| A6 | a3 | 42.1 | b4 | 57.5 | 1.02:1 | c1 | 0.4 | 1.465 |

Preparation of the Photopolymer Formulation without Photoinitiator for Determining the Plateau Modulus $G_0$.

Table 2 lists the investigated examples of the photopolymer formulations for determining the plateau modulus $G_0$, which do not have an exclusive character in their composition. These photopolymer formulations were prepared according to the method which was described in the section on the measurement of the plateau modulus $G_0$ of the photopolymers by means of an oscillation rheometer.

TABLE 2

Photopolymer formulations which were investigated with regard to their plateau modulus $G_0$ and their crosslinking density $1/M_C$.

| Photopolymer formulation without photoiniator | Isocyanate component | Proportion (gr) | Isocyanate-reactive component | Proportion (gr) | NCO:OH | Radiation-curing component | Proportion by (% weight) | Catalyst in solution | Proportion (gr) |
|---|---|---|---|---|---|---|---|---|---|
| F1 | a1 | 2.432 | b1 | 6.566 | 1.02:1 | B3 | 12.5 | c1 | 0.0107 |
| F2 | a1 | 2.027 | b1 | 5.472 | 1.02:1 | B3 | 25.0 | c1 | 0.0106 |
| F3 | a1 | 1.406 | b2 | 7.593 | 1.02:1 | B3 | 12.5 | c1 | 0.0104 |
| F4 | a1 | 1.172 | b2 | 6.328 | 1.02:1 | B2 | 25.0 | c1 | 0.0104 |
| F5 | a1 | 1.172 | b2 | 6.328 | 1.02:1 | B3 | 25.0 | c1 | 0.0104 |
| F6 | a1 | 1.063 | b2 | 6.437 | 1:0.90 | B3 | 25.0 | c1 | 0.0100 |
| F7 | a3 | 3.202 | b4 | 4.295 | 1.02:1 | B3 | 25.0 | c1 | 0.0328 |
| F8 | a3 | 0.725 | b5 | 6.773 | 1.02:1 | B3 | 25.0 | c1 | 0.0331 |
| F9 | a3 | 5.510 | b3 | 1.987 | 1.02:1 | B3 | 25.0 | c1 | 0.0318 |

TABLE 2-continued

Photopolymer formulations which were investigated with regard to their plateau modulus $G_0$ and their crosslinking density $1/M_C$.

| Photopolymer formulation without photoiniator | Isocyanate component | Proportion (gr) | Isocyanate-reactive component | Proportion (gr) | NCO:OH | Radiation-curing component | Proportion by (% weight) | Catalyst in solution | Proportion (gr) |
|---|---|---|---|---|---|---|---|---|---|
| F10 | a3 | 1.722 | b3 | 4.775 | 1.02:1 | B3 | 35.0 | c1 | 0.0300 |
| F11 | a4 | 4.223 | b3 | 2.310 | 1.02:1 | B3 | 22.5 | c1 | 0.0664 |
| F12 | a1 | 1.117 | b2 | 6.031 | 1.02:1 | B4 | 25.0 | c1 | 0.0080 |
| F13 | a3 | 1.960 | b3 | 5.187 | 1.02:1 | B4 | 25.0 | c1 | 0.0180 |
| F14 | a1 | 1.117 | b2 | 6.023 | 1.02:1 | B1 | 25.0 | c1 | 0.0111 |
| F17 | a2 | 1.361 | b4 | 6.161 | 1.02:1 | B3 | 20.0 | c1 | 0.0201 |

Production of the Holographic Media Based on Photopolymer Formulation with Photoinitiator for Determining the Performance Parameters E and Δn.

The photopolymer formulations were used for producing holographic media (cf. Table 3) in which the photopolymer was produced as a layer between glass plates of 1 mm thickness each. This type of holographic media is particularly suitable for determining their performance by the method described in the section on measurement of the holographic properties DE and Δn of the holographic media by means of two-beam interference in a reflection arrangement and is therefore, in the context of the formulated claims, not meant to be limited to the holographic media, provided that the photopolymer formulation used satisfies the claimed properties with regard to plateau modulus $G_0$ and/or $Q = M_C/M_{Mo}$.

Exemplary Production of the Holographic Media

For the production of the holographic media, component B), component C) (which may already be predissolved in component B)) and optionally the additives are dissolved in the isocyanate-reactive component b), optionally at 60° C., in the dark, after which glass beads measuring 20 μm (e.g. from Whitehouse Scientific Ltd, Waverton, Chester, CH3 7PB, United Kingdom) are added and thoroughly mixed (Speedmixer). Heating to 60° C. for not more than 10 minutes in a drying oven is optionally effected. Thereafter, the isocyanate component a) is added and mixing is effected again in the Speedmixer for 1 minute. Subsequently, a solution of component c) is added and mixing is effected in the Speedmixer again for 1 minute. The mixture obtained is degassed with stirring at <1 mbar for not more than 30 seconds, after which it is distributed on glass plates measuring 50×75 mm and these are each covered with a further glass plate. The curing of the PU formulation takes place under 15 kg weights over several hours (usually overnight). In some cases, the media are postcured in a light-tight packaging for a further 2 hours at 60° C. Since different formulations having different initial viscosity and different curing rate of the matrix do not always lead to the same layer thicknesses d of the photopolymer layer, d is determined separately from the characteristics of the holograms written for each sample.

TABLE 3

Holographic media which were tested with regard to their performance Δn and E.

| Holographic medium | Isocyanate component | Proportion (gr) | Isocyanate-reactive component | Proportion (gr) | NCO:OH | Radiation-curable component | Proportion (% by weight) | Photo-initiator | Proportion (% by weight) | Catalyst solution | Proportion (gr) | Corresponds to photopolymer formulation without photoinitiator |
|---|---|---|---|---|---|---|---|---|---|---|---|---|
| M1 | a1 | 20.5 | b1 | 55.7 | 1.02:1 | B3 | 12.5 | C1 | 4.6 | c1 | 0.0060 | F1 |
| M2 | a1 | 18.8 | b1 | 51.3 | 1.02:1 | B3 | 25.0 | C1 | 4.6 | c1 | 0.0040 | F2 |
| M3 | a1 | 12.9 | b2 | 69.7 | 1.02:1 | B3 | 12.5 | C1 | 4.6 | c1 | 0.0090 | F3 |
| M4 | a1 | 22.2 | b2 | 72.9 | 1.02:1 | B2 | 25.0 | C1 | 4.6 | c1 | 0.0060 | F4 |
| M5 | a1 | 11.0 | b2 | 59.3 | 1.02:1 | B3 | 25.0 | C1 | 4.6 | c1 | 0.0060 | F5 |
| M6 | a1 | 10.0 | b2 | 60.3 | 1:0.90 | B3 | 25.0 | C1 | 4.6 | c1 | 0.0060 | F6 |
| M7 | a3 | 29.9 | b4 | 40.1 | 1.02:1 | B3 | 25.0 | C1 | 4.6 | c1 | 0.0446 | F7 |
| M8 | a2 | 6.8 | b5 | 63.3 | 1.02:1 | B3 | 25.0 | C1 | 4.6 | c1 | 0.0363 | F8 |
| M9 | a3 | 18.6 | b3 | 51.4 | 1.02:1 | B3 | 25.0 | C1 | 4.6 | c1 | 0.0315 | F9 |
| M10 | a3 | 15.9 | b3 | 44.2 | 1.02:1 | B3 | 35.0 | C1 | 4.6 | c1 | 0.0360 | F10 |
| M11 | a4 | 38.5 | b3 | 31.6 | 1.02:1 | B3 | 22.5 | C1 | 4.6 | c1 | 0.0275 | F11 |
| M12 | a1 | 11.0 | b2 | 59.3 | 1.02:1 | B4 | 25.0 | C1 C2 | 4.6 4.6 | c1 | 0.0090 | F12 |
| M13 | a3 | 19.2 | b3 | 50.9 | 1.02:1 | B4 | 25.0 | C2 | 4.6 | c1 | 0.0300 | F13 |
| M14 | a1 | 11.0 | b2 | 59.3 | 1.02:1 | B1 | 25.0 | C1 | 4.6 | c1 | 0.0060 | F14 |
| M17 | a2 | 13.6 | b4 | 61.5 | 1.02:1 | B3 | 20.0 | C1 | 4.6 | c1 | 0.0336 | F17 |

Results from $G_0$, $M_C$, $M_{Mo}$ and Δn Combined.

The following measured values for $G_0$ (MPa), $M_C$ (g/mol), $Q = M_C/M_{Mo}$, and Δn at the dose E (mJ/cm$^2$) were obtained and are shown in Table 4:

TABLE 4

Evaluation of selected examples. The values characterized by * were measured with λ = 532 nm instead of with λ = 633 nm.

| Example type | Holographic medium | Δn | E | NCO:OH | Corresponding photopolymer formulation without photoinitiator | $G_0$ | $M_C$ | $Q = M_C/M_{Mo}$ | $n_{Mo} - n_{Ma}$ | Corresponding matrix |
|---|---|---|---|---|---|---|---|---|---|---|
| Comparison | M1 | 0.0062 | 8.1 | 1.02:1 | F1 | 2.25 | 1194 | 1.47 | 0.094 | A1 |
| Comparison | M2 | 0.0059 | 15.9 | 1.02:1 | F2 | 1.75 | 1535 | 1.89 | 0.094 | A1 |
| Comparison | M3 | 0.0070 | 15.9 | 1.02:1 | F3 | 1.60 | 1678 | 2.06 | 0.103 | A2 |
| Comparison | M4 | 0.0059 | 36.9 | 1.02:1 | F4 | 1.35 | 1989 | 1.21 | 0.127 | A2 |
| according to the invention | M5 | 0.0101 | 7.8 | 1.02:1 | F5 | 0.80 | 3357 | 4.13 | 0.103 | A2 |
| according to the invention | M6 | 0.0113 | 9.1 | 1:0.90 | F6 | 0.70 | 3836 | 4.72 | 0.103 | A2 |
| according to the invention | M7 | 0.0130 | 8.9 | 1.02:1 | F7 | 0.70 | 3836 | 4.72 | 0.114 | A6 |
| according to the invention |  | 0.0118 | 18.2 |  |  |  |  |  |  |  |
| according to the invention | M12 | 0.0110* | 127.3* | 1.02:1 | F12 | 0.53 | 5067 | 18.03 | 0.098 | A2 |
| according to the invention | M17 | 0.0130 | 9.1 | 1.02:1 | F17 | 0.43 | 6231 | 7.66 | 0.109 | A3 |
| according to the invention | M14 | 0.0103 | 18.3 | 1.02:1 | F14 | 0.36 | 7460 | 15.94 | 0.065 | A2 |
| according to the invention | M8 | 0.0147 | 9.1 | 1.02:1 | F8 | 0.30 | 8951 | 11.01 |  |  |
| according to the invention | M9 | 0.0170 | 9.1 | 1.02:1 | F9 | 0.25 | 10742 | 13.21 | 0.124 | A5 |
| according to the invention | M10 | 0.0208 | 4.5 | 1.02:1 | F10 | 0.24 | 11189 | 13.76 | 0.124 | A5 |
| according to the invention | M13 | 0.011* | 63.7* | 1.02:1 | F13 | 0.10 | 26854 | 95.57 | 0.121 | A5 |
| according to the invention | M11 | 0.0171 | 4.7 | 1.02:1 | F11 | 0.05 | 53708 | 66.06 |  |  |

The Δn values found for the holographic media surprisingly show that photopolymer formulations whose plateau modulus $G_0$ is less than 1.0 MPa or whose equivalent average molecular weight $M_C$ of the segments bridging two polymer strands is greater than 2685 g/mol, particularly preferably whose ratio $M_C/M_{Mo}$, is greater than 3.30, are very suitable for use in holographic media since □n values greater than 0.010 are reached.

Moreover, they show that this design criterion for photopolymer formulations has the same or even greater significance than the refractive index difference between matrix and photopolymerizable monomers (cf. for example M14 in comparison with M7 or with M4) or that this design criterion further improves in their performance existing photopolymer formulations in which this index difference is fixed (cf. for example M6 in comparison with M5 or with M3).

The invention claimed is:

1. A photopolymer formulation comprising a three-dimensionally crosslinked organic polymer A) or the precursors thereof as a matrix, a compound B) comprising groups that react with ethylenically unsaturated compounds via polymerization under the action of actinic radiation and is present in solution or dispersion in said matrix, and C) at least one photoinitiator, wherein the network density of said three-dimensionally crosslinked organic polymer, expressed as the average molecular weight $M_C$ of the segments bridging two polymer strands, is at least 2685 g/mol, wherein the ratio Q of the molecular weight $M_C$ to the number average molecular weight $M_{Mo}$ of B) is greater than 3.30, wherein a cured composition prepared from the photopolymer formulation has a plateau modulus $G_0$ of greater than 0.05 MPa and less than 1.0 MPa, wherein the plateau modulus $G_0$ is determined by measuring the curing of the matrix in an oscillation rheometer as follows:

plate spacing 250 μm, oscillation measuring mode at a constant angular frequency $\omega_0$ of 10 rad/s and a controlled logarithmic deformation amplitude ramp of 1% temperature 50° C., normal force regulation set at 0 Newton recording of the storage modulus G' over the measuring time for at least 2 hours or until a constant value of $G_{max}$ of G' was reached; this value is referred to as $G_0$.

2. The photopolymer formulation of claim 1, wherein the network density of said three-dimensionally crosslinked organic polymer is in the range of from 7500 to 55000 g/mol.

3. The photopolymer formulation of claim 1, wherein the ratio Q is greater than 10.00.

4. The photopolymer formulation of claim 1, wherein said three-dimensionally crosslinked organic polymers comprise urethane groups.

5. The photopolymer formulation of claim 1, wherein said three-dimensionally crosslinked organic polymers are composed of an isocyanate component a) and an isocyanate-reactive component b).

6. The photopolymer formulation of claim 1, wherein A) comprises an isocyanate component a) and an isocyanate-reactive component b).

7. The photopolymer formulation of claim 6, wherein component a) comprises a polyisocyanate based on HDI with isocyanurate and/or iminooxadiazinedione structures or a prepolymer having an NCO functionality of from 2 to 5 with allophanate and/or urethane structures based on HDI and/or TMDI and a polyether polyol, polyester polyol, and/or polycarbonate polyol.

8. The photopolymer formulation of claim 7, wherein the polyisocyanates has a residual contents of free monomeric isocyanate of less than 1% by weight.

9. The photopolymer formulation of claim 6, wherein component b) comprises a polypropylene oxide, a polyethylene oxide, and/or combinations thereof in the form of a random or block copolymer and/or a block copolymer of the abovementioned type which additionally comprises tetrahydrofuran, butylene oxide, ors caprolactone as monomer units, wherein the OH functionality is from 1.5 to 6 and the number average molecular weight is from 200 to 18000 g/mol.

10. The photopolymer formulation of claim 1, wherein said compound of B) has a refractive index $n_D 20$ of greater than 1.54.

11. The photopolymer formulation of claim 1, wherein said compound of B) comprise acrylate and/or methacrylate groups as radiation-curing groups.

12. A medium suitable for recording visual holograms produced from the photopolymer formulation of claim 1.

13. An optical element, image, or representation produced from the medium of claim 12.

14. A method for exposing the medium of claim 12 comprising selectively polymerizing writing monomers with actinic radiation.

15. A method for preparing a photopolymer formulation comprising mixing a three-dimensionally crosslinked organic polymer A) or the precursors thereof as a matrix, a compound B) comprising groups that react with ethylenically unsaturated compounds via polymerization under the action of actinic radiation and is present in solution or dispersion in said matrix, and C) at least one photoinitiator, and optionally catalysts, free radical stabilizers, solvents, additives and other auxiliaries and/or additives, wherein the components chosen for the photopolymer formulation are only compounds wherein the network density of said three-dimensionally crosslinked organic polymer, expressed as the average molecular weight $M_C$ of the segments bridging two polymer strands, is at least 2685 g/mol, wherein the ratio Q of the molecular weight $M_C$ to the number average molecular weight $M_{Mo}$ of B) is greater than 3.30, and determining a plateau modulus $G_0$ by measuring the curing of the matrix in an oscillation rheometer as follows:

plate spacing 250 µm, oscillation measuring mode at a constant angular frequency $\omega_0$ of 10 rad/s and a controlled logarithmic deformation amplitude ramp of 1% temperature 50° C., normal force regulation set at 0 Newton recording of the storage modulus G' over the measuring time for at least 2 hours or until a constant value of $G_{max}$ of G' was reached; this value is referred to as $G_0$, wherein the cured composition prepared from the photopolymer formulation has a plateau modulus $G_0$ of greater than 0.05 MPa and less than 1.0 MPa.

* * * * *